US011457801B2

(12) United States Patent
Kikuchi et al.

(10) Patent No.: US 11,457,801 B2
(45) Date of Patent: Oct. 4, 2022

(54) IMAGE PROCESSING DEVICE, IMAGE PROCESSING METHOD, AND ENDOSCOPE SYSTEM

(71) Applicant: SONY CORPORATION, Tokyo (JP)

(72) Inventors: Daisuke Kikuchi, Kanagawa (JP); Akio Furukawa, Tokyo (JP); Masayoshi Akita, Tokyo (JP); Mitsunori Ueda, Tokyo (JP); Hiroshi Ichiki, Kanagawa (JP); Tsuneo Hayashi, Tokyo (JP); Yuki Sugie, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 765 days.

(21) Appl. No.: 16/316,134

(22) PCT Filed: Jul. 12, 2017

(86) PCT No.: PCT/JP2017/025462
§ 371 (c)(1),
(2) Date: Jan. 8, 2019

(87) PCT Pub. No.: WO2018/021035
PCT Pub. Date: Feb. 1, 2018

(65) Prior Publication Data
US 2021/0282630 A1 Sep. 16, 2021

(30) Foreign Application Priority Data
Jul. 26, 2016 (JP) .............................. JP2016-145905

(51) Int. Cl.
*A61B 1/06* (2006.01)
*A61B 1/00* (2006.01)
(Continued)

(52) U.S. Cl.
CPC ........ *A61B 1/0661* (2013.01); *A61B 1/00009* (2013.01); *A61B 1/00018* (2013.01);
(Continued)

(58) Field of Classification Search
CPC . A61B 1/0661; A61B 1/00009; H04N 5/2353
(Continued)

(56) References Cited

U.S. PATENT DOCUMENTS 9,186,054 B2    11/2015 Godo et al.
2010/0069713 A1*  3/2010 Endo .................... H04N 5/2354
                                                            600/109
(Continued)

FOREIGN PATENT DOCUMENTS

CN    102301212 A    12/2011
CN    103096781 A     5/2013
(Continued)

OTHER PUBLICATIONS

Office Action for JP Patent Application No. 2018-529759 dated Jan. 26, 2021.
(Continued)

*Primary Examiner* — Jeffery A Williams
(74) *Attorney, Agent, or Firm* — Chip Law Group

(57) ABSTRACT

The present technology relates to an image processing device, an image processing method, an endoscope system, and a program that enable motion detection with higher accuracy. The endoscope system includes: a light source capable of performing a pulsed-light emission; a light-source control unit that controls the light source such that the light source performs the pulsed-light emission a plurality of times in an exposure time period of each captured image; an imaging unit that takes the captured images; and a motion detection unit that detects a motion of a photographic subject in the captured images. The present technology is applicable to the endoscope system.

18 Claims, 23 Drawing Sheets

(51) Int. Cl.
    *H04N 5/00*     (2011.01)
    *H04N 5/232*     (2006.01)
    *H04N 5/235*     (2006.01)
    *H04N 5/225*     (2006.01)

(52) U.S. Cl.
    CPC ....... *H04N 5/2353* (2013.01); *H04N 5/23267* (2013.01); *H04N 2005/2255* (2013.01)

(58) Field of Classification Search
    USPC .......................................................... 348/68
    See application file for complete search history.

(56) References Cited

U.S. PATENT DOCUMENTS

| | | |
|---|---|---|
| 2011/0249864 A1 | 10/2011 | Venkatesan et al. |
| 2012/0019654 A1 | 1/2012 | Venkatesan et al. |
| 2012/0116157 A1* | 5/2012 | Seto ................... A61B 1/0638 600/109 |
| 2012/0262559 A1* | 10/2012 | On ..................... H04N 5/23267 348/65 |
| 2013/0165753 A1 | 6/2013 | Takahashi |

FOREIGN PATENT DOCUMENTS

| | | |
|---|---|---|
| CN | 104080392 A | 10/2014 |
| EP | 2375227 A1 | 10/2011 |
| EP | 2796085 A1 | 10/2014 |
| JP | 63-298065 A | 12/1988 |
| JP | 01-158930 A | 6/1989 |
| JP | 08-122354 A | 5/1996 |
| JP | 10-201707 A | 8/1998 |
| JP | 10-221201 A | 8/1998 |
| JP | 11-64359 A | 3/1999 |
| JP | 2002-148270 A | 5/2002 |
| JP | 2002-253494 A | 9/2002 |
| JP | 2003-032529 A | 1/2003 |
| JP | 2010-117190 A | 5/2010 |
| JP | 2011-221024 A | 11/2011 |
| JP | 2012-055498 A | 3/2012 |
| JP | 2012-119726 A | 6/2012 |
| JP | 2012-516432 A | 7/2012 |
| JP | 2014-073398 A | 4/2014 |
| JP | 2016-096848 A | 5/2016 |
| JP | 2016-202380 A | 12/2016 |
| WO | 2010/086044 A1 | 8/2010 |
| WO | 2010/092728 A1 | 8/2010 |
| WO | 2012/032914 A1 | 3/2012 |
| WO | 2013/121616 A1 | 8/2013 |

OTHER PUBLICATIONS

Varun, et al., "Color plane slicing and its applications to motion characterization for machine vision", 2009 IEEE/ASME International Conference on Advanced Intelligent Mechatronics, Suntec Convention and Exhibition Center Singapore, Jul. 14-17, 2009, pp. 590-594.

Office Action for JP Patent Application No. 2018-529759, dated Nov. 5, 2020, 11 pages of Office Action and 16 pages of English Translation.

International Search Report and Written Opinion of PCT Application No. PCT/JP2017/025462, dated Oct. 17, 2017, 3 pages of translation and 13 pages of ISRWO.

Varun, et al., "Color Plane Slicing and its Applications to Motion Characterization for Machine Vision", 2009 IEEE/ASME International Conference on Advanced Intelligent Mechatronics, Jul. 14-17, 2009. Abstract only.

* cited by examiner

IMAGE PROCESSING DEVICE, IMAGE PROCESSING METHOD, AND ENDOSCOPE SYSTEM

CROSS REFERENCE TO RELATED APPLICATIONS

This application is a U.S. National Phase of International Patent Application No. PCT/JP2017/025462 filed on Jul. 12, 2017, which claims priority benefit of Japanese Patent Application No. JP 2016-145905 filed in the Japan Patent Office on Jul. 26, 2016. Each of the above-referenced applications is hereby incorporated herein by reference in its entirety.

TECHNICAL FIELD

The present technology relates to an image processing device, an image processing method, an endoscope system, and a program. More particularly, the present technology relates to an image processing device, an image processing method, an endoscope system, and a program that enable motion detection with higher accuracy.

BACKGROUND ART

Hitherto, in an endoscope device, in order that observation is performed with higher accuracy, motion detection may be used in combination with imaging of a photographic subject.

As an example of technologies that use the motion detection, there may be mentioned a technology including detecting motions of the photographic subject and a camera, and utilizing these motions for image stabilization. As another example, there may be mentioned a technology including detecting periodical motions of the photographic subject, such as pulsation, acquiring images in-phase with each other on the basis of results of the detection, and outputting and displaying unblurred in-phase images. Further, as still another example, a technology including detecting the motion of the photographic subject, and applying a result of the detection to scene recognition has also been proposed.

As a technology for performing such motion detection, a method including detecting a motion from a plurality of previous frames, and imaging and displaying a result of the detection has been proposed (refer, for example, to Patent Literature 1).

CITATION LIST

Patent Literature

Patent Literature 1: Japanese Patent Application Laid-open No. 2011-172783

DISCLOSURE OF INVENTION

Technical Problem

However, in the above-described technology, there are difficulties in detecting the motion with high accuracy.

For example, in the method including using images corresponding to the plurality of frames, information items of two or more previous frames are needed to calculate the motion. Thus, a motion information item to be obtained is calculated from relatively old information items such as that of a penultimate frame. Therefore, a motion in a current frame cannot be estimated with sufficient accuracy. In other words, at a time of using the motion information item for image correction processes such as the image stabilization, a mismatch occurs between a detected motion and an actual motion in the current motion to which the result of the motion detection is applied.

Further, in the method including using the images corresponding to the plurality of frames, the motion detection cannot be performed with respect to motions that fluctuate at a rate higher than frame intervals, and to vibrating motions in short periods. In addition, even in a case where a motion between frames can be detected, when the motion is rapid, motion blurring occurs in images. Thus, inter-frame image mismatches occur to decrease accuracy in motion detection.

The present technology has been made in view of such circumstances so as to enable motion detection with higher accuracy.

Solution to Problem

According to a first aspect of the present technology, there is provided an image processing device including:

a light-source control unit that controls a light source such that the light source performs a pulsed-light emission a plurality of times in an exposure time period of each captured image; and a motion detection unit that detects a motion of a photographic subject in the captured images.

The captured images may be images of a living body.

The motion detection unit may be caused to detect, as the motion, magnitudes of components of a motion vector on the basis of one of the captured images.

The light-source control unit may be caused to control the light source such that the light source outputs light beams containing the same wavelength component at times of the pulsed-light emissions.

The motion detection unit may be caused to further detect, as the motion, a direction of the motion vector on the basis of a plurality of the captured images.

The image processing device may further include
a motion correction unit that performs motion correction with respect to the captured images on the basis of a result of the detection of the motion.

The image processing device may further include
an image generation unit that generates images of the photographic subject from other ones of the captured images on the basis of a result of the detection of the motion, the other ones of the captured images being at time points when the motion is not made.

The light-source control unit may be caused to control the light source such that exposure time periods in each of which the light beam containing the wavelength component is continuously output, and other exposure time periods in each of which the pulsed-light emission is performed the plurality of times are provided.

The motion detection unit may be caused to detect the motion on the basis of ones of the captured images, the ones of the captured images corresponding to the other exposure time periods in each of which the pulsed-light emission is performed the plurality of times.

The image processing device may further include
a motion correction unit that performs motion correction with respect to other ones of the captured images on the basis of a result of the detection of the motion, the other ones of the captured images corresponding to the exposure time periods in each of which the light beam containing the wavelength component is continuously output.

The light-source control unit may be caused to control the light source such that the exposure time periods in each of which the light beam containing the wavelength component is continuously output, and the other exposure time periods in each of which the pulsed-light emission is performed the plurality of times are provided alternately to each other.

The light-source control unit may be caused to control the light source such that the other exposure time periods in each of which the pulsed-light emission is performed the plurality of times are provided at unequal intervals.

The light-source control unit may be caused to control the light source such that the light source outputs light beams containing wavelength components different from each other respectively at times of the plurality of times of pulsed-light emissions.

The motion detection unit may be caused to detect, as the motion, a motion vector on the basis of images respectively containing the wavelength components, the images respectively containing the wavelength components being obtained from one of the captured images.

The light-source control unit may be caused to control another light source different from the light source such that the other light source continuously outputs a light beam containing a predetermined wavelength component during an exposure time period of each input image of the photographic subject, the input images being different from the captured images, and to control the light source such that the light source outputs light beams containing another wavelength component different from the predetermined wavelength component by performing the pulsed-light emission the plurality of times in a time period including at least a part of the exposure time period of each of the input images.

The image processing device may further include
a first imaging unit that takes the captured images,
a second imaging unit that takes the input images, and
a splitting element that
optically splits the light beams from the photographic subject,
inputs ones of the split light beams to the first imaging unit, and
inputs other ones of the split light beams to the second imaging unit.

The image processing device may further include
a motion correction unit that performs motion correction with respect to the input images on the basis of a result of the detection of the motion.

The light-source control unit may be caused to control the light source such that the light source performs the pulsed-light emissions in a plurality of different periods while changing periods of the pulsed-light emissions.

The motion detection unit may be caused to detect, as the motion, a vibration period of the photographic subject on the basis of degrees of contrasts of the captured images obtained respectively in the plurality of different periods.

The light-source control unit may be caused to cause, after the detection of the motion, the light source to perform the pulsed-light emissions in a period in accordance with a result of the detection of the motion.

According to the first aspect of the present technology, there is provided an image processing method or a program including the steps of:

controlling a light source such that the light source performs a pulsed-light emission a plurality of times in an exposure time period of each captured image; and detecting a motion of a photographic subject in the captured images.

According to the first aspect of the present technology, the light source is controlled to perform the pulsed-light emission the plurality of times in the exposure time period of each of the captured images, and the motion of the photographic subject in the captured images is detected.

According to a second aspect of the present technology, there is provided an endoscope system including:

a light source capable of performing a pulsed-light emission;

a light-source control unit that controls the light source such that the light source performs the pulsed-light emission a plurality of times in an exposure time period of each captured image;

an imaging unit that takes the captured images; and a motion detection unit that detects a motion of a photographic subject in the captured images.

According to the second aspect of the present technology, the light source is controlled to perform the pulsed-light emission the plurality of times in the exposure time period of each of the captured images, the captured images are taken, and the motion of the photographic subject in the captured images is detected.

Advantageous Effects of Invention

According to the first aspect and the second aspect of the present technology, the motion detection can be performed with higher accuracy.

Note that, the advantages disclosed herein are not necessarily limited to those described hereinabove, and all the advantages described hereinabove and hereinbelow can be obtained.

MODE(S) FOR CARRYING OUT THE INVENTION

Now, with reference to the drawings, embodiments to which the present technology is applied are described.

First Embodiment

<Configuration Example of Endoscope System>

Figure 1:
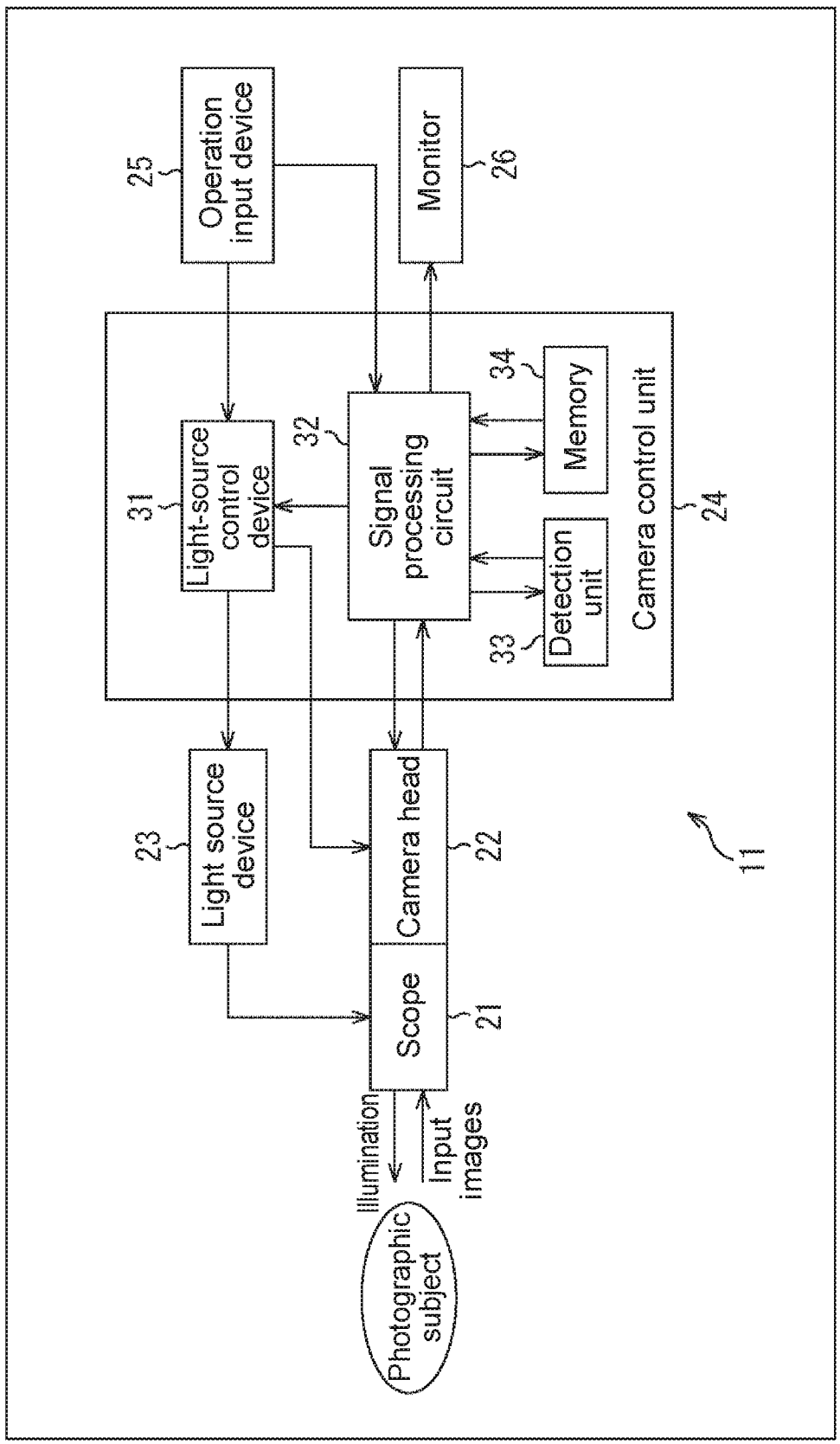
FIG. 1 A diagram showing a configuration example of an endoscope system.

FIG. 1 is a diagram showing a configuration example of an embodiment of an endoscope system to which the present technology is applied.

An endoscope system 11 shown in FIG. 1 includes a scope 21, a camera head 22, a light source device 23, a camera control unit 24, an operation input device 25, and a monitor 26. Note that, in the following, the camera control unit 24 is referred to also as a CCU (Camera Control Unit) 24 as appropriate.

This endoscope system 11, which is used mainly in the medical field, is a system that functions as an endoscope device that causes the scope 21 to be inserted into a participant, and takes images of arbitrary parts (surgical parts) in the participant as images of a surgical field. Note that, in the following, description is made by way of an example in which a photographic subject is the participant such as a patient, but, as a matter of course, the photographic subject to be an imaging target in the endoscope system 11 may be a living body other than humans.

The scope 21 is a lens barrel portion that includes an optical system constituted by lenses such as an objective lens, and that is inserted into the participant. The scope 21 applies illumination light beams input from the light source device 23 to the photographic subject. The scope 21 converges incident reflected-light beams from the photographic subject, and guides the converged reflected-light beams to the camera head 22.

Specifically, when the illumination light beams are applied from the scope 21 to the photographic subject, these illumination light beams turn into the reflected light beams by being reflected by the photographic subject. The scope 21 converges and inputs the reflected light beams into the camera head 22. Note that, the scope 21 may be a flexible lens barrel, or may be a rigid lens barrel.

The camera head 22, which is provided integrally with the scope 21, is constituted, for example, by a camera, more specifically, by an imaging element or the like. Under control by the CCU 24, the camera head 22 captures the photographic subject by receiving and photoelectrically converting the incident reflected-light beams from the scope 21, and supplies image data items of resultant input images to the CCU 24. Such input images are, for example, the images of the photographic subject, specifically, images of the surgical field at a time of performing surgery or the like, more specifically, images of the living body such as the patient.

The light source device 23, which is constituted, for example, by a laser light source or an LED (Light Emitting Diode) light source, outputs light beams in a specific wavelength band as the illumination light beams under the control by the CCU 24, and inputs these illumination light beams to the scope 21. For example, from the light source device 23, white light beams or the like are output as the illumination light beams.

The CCU 24 control operations of an entirety of the endoscope system 11. The CCU 24 includes a light-source control device 31, a signal processing circuit 32, a detection unit 33, and a memory 34.

Under control by the signal processing circuit 32, the light-source control device 31 controls the application of the illumination light beams by the light source device 23, that is, ON/OFF of the illumination light beams. Specifically, the light-source control device 31 controls, for example, irradiation timings and irradiation time periods of the illumination light beams, and light intensity of the illumination light beams.

Further, the light-source control device 31 supplies synchronizing signals for synchronizing an illumination operation by the light source device 23, and the imaging operation by the camera head 22 with each other to the camera head 22.

The signal processing circuit 32 supplies the input images supplied from the camera head 22 to the detection unit 33, and causes the detection unit 33 to detect predetermined features. In addition, the signal processing circuit 32 generates appropriate signal-processing parameters on the basis of detection results supplied from the detection unit 33 and of data items recorded in the memory 34. Further, on the basis of the signal-processing parameters, the signal processing circuit 32 executes a predetermined signal process on the input images supplied from the camera head 22, and supplies resultant output images to the monitor 26.

The detection unit 33 detects, from the input images supplied from the signal processing circuit 32, the predetermined features such as a motion of the photographic subject in the input images, and supplies the results of the detection to the signal processing circuit 32.

The memory 34 records, for example, various data items such as prepared conversion parameters, and the signal-processing results supplied from the signal processing circuit 32, and supplies, for example, data items recorded therein to the signal processing circuit 32.

The operation input device 25, which includes buttons, switches, or a touchscreen superimposed on the monitor 26, is operated by a user who operates the endoscope system 11. The operation input device 25 supplies signals in response to the operations by the user to the signal processing circuit 32 and the light-source control device 31.

The monitor 26, which is constituted, for example, by a liquid-crystal display panel, displays the output images supplied from the signal processing circuit 32.

<Functional Configuration Example of Endoscope System>

Figure 2:
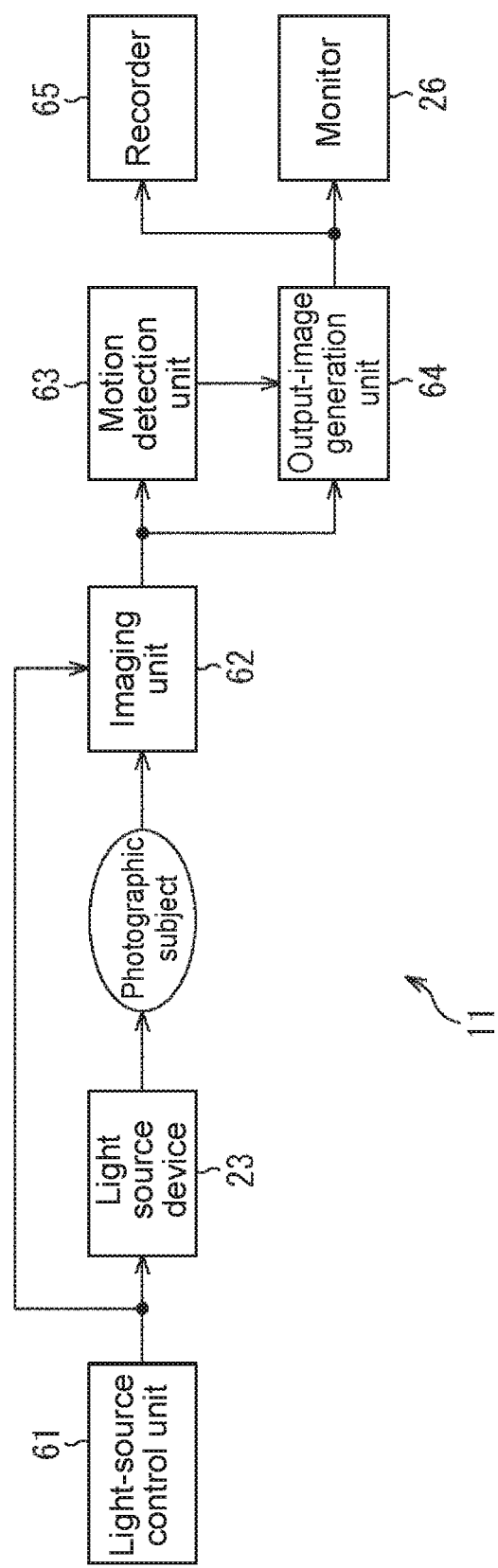
FIG. 2 A diagram showing a functional configuration example of the endoscope system.

Next, a functional configuration example of the endoscope system 11 shown in FIG. 1 is described. FIG. 2 is a diagram showing the functional configuration example of the endoscope system 11. Note that, in FIG. 2, components corresponding to those in the case of FIG. 1 are denoted by the same reference symbols, and description thereof is omitted as appropriate.

The endoscope system 11 shown in FIG. 2 includes a light-source control unit 61, the light source device 23, an imaging unit 62, a motion detection unit 63, an output-image generation unit 64, the monitor 26, and a recorder 65.

The light-source control unit 61, which corresponds, for example, to the light-source control device 31 shown in FIG. 1, supplies the synchronizing signals for synchronizing the application of the illumination light beams and the taking of the input images with each other to the light source device 23 and the imaging unit 62.

The light source device 23 performs pulsed-light emissions at predetermined timings in response to the synchronizing signals supplied from the light-source control unit 61 so that the illumination light beams are applied to the photographic subject. When the illumination light beams are applied to the photographic subject, these illumination light beams turn into the reflected light beams by being reflected by the photographic subject, and then are received by the imaging unit 62.

The imaging unit 62, which is constituted by the camera head 22 shown in FIG. 1, captures the photographic subject as captured images to be the input images in response to the synchronizing signals supplied from the light-source control unit 61, and supplies these input images to the motion detection unit 63 and the output-image generation unit 64. In other words, the imaging unit 62 includes the imaging element constituting the camera, and obtains the input images by receiving and photoelectrically converging the reflected light beams from the photographic subject.

The motion detection unit 63 detects the motion of the photographic subject in the input images on the basis of the input images supplied from the imaging unit 62, and supplies, for example, resultant motion vectors as motion information items indicating detection results of the motion of the photographic subject to the output-image generation unit 64. The detection unit 33 of FIG. 1 serves as the motion detection unit 63, for example.

On the basis of the motion information items supplied from the motion detection unit 63, the output-image generation unit 64 performs motion correction such as image stabilization with respect to the input images supplied from the imaging unit 62. Then, the output-image generation unit 64 supplies the resultant output images to the monitor 26 and the recorder 65. The signal processing circuit 32 of FIG. 1 serves as the output-image generation unit 64, for example. When the output-image generation unit 64 performs the motion correction such as the image stabilization in this way, the output-image generation unit 64 functions as a motion correction unit.

The recorder 65, which is constituted, for example, by a nonvolatile recording unit (not shown in FIG. 1) connected to the signal processing circuit 32 of FIG. 1, records the output images supplied from the output-image generation unit 64. Further, the monitor 26 displays the output images supplied from the output-image generation unit 64.

<Processes in Endoscope System>

Next, an example of specific processes in the endoscope system 11 shown in FIG. 2 is described.

As the light source device 23, for example, a laser light source that is capable of performing the pulsed-light emissions and emits RGB white-light beams is used.

In such a case, the light source device 23 includes an "R" light source that outputs a narrow-wavelength light beam containing a wavelength component of R (red), a "G" light source that outputs a narrow-wavelength light beam containing a wavelength component of G (green), a "B" light source that outputs a narrow-wavelength light beam containing a wavelength component of B (blue), and a synthetic optical system that synthesizes with each other and outputs the light beams output from these light sources.

Thus, when the white light beam is output as the illumination light beam from the light source device 23, the light beams to be output simultaneously with each other from the "R" light source, the "G" light source, and the "B" light source, that is, the light beam containing the "R" component, the light beam containing the "G" component, and the light beam containing the "B" component are synthesized with each other by the synthetic optical system, and then output from the light source device 23. Note that, although the illumination light beam, which contains a predetermined wavelength component and is output from the light source device 23, is the white light beam in the description of this example, the illumination light beam may be a light beam in any wavelength band.

Figure 3:
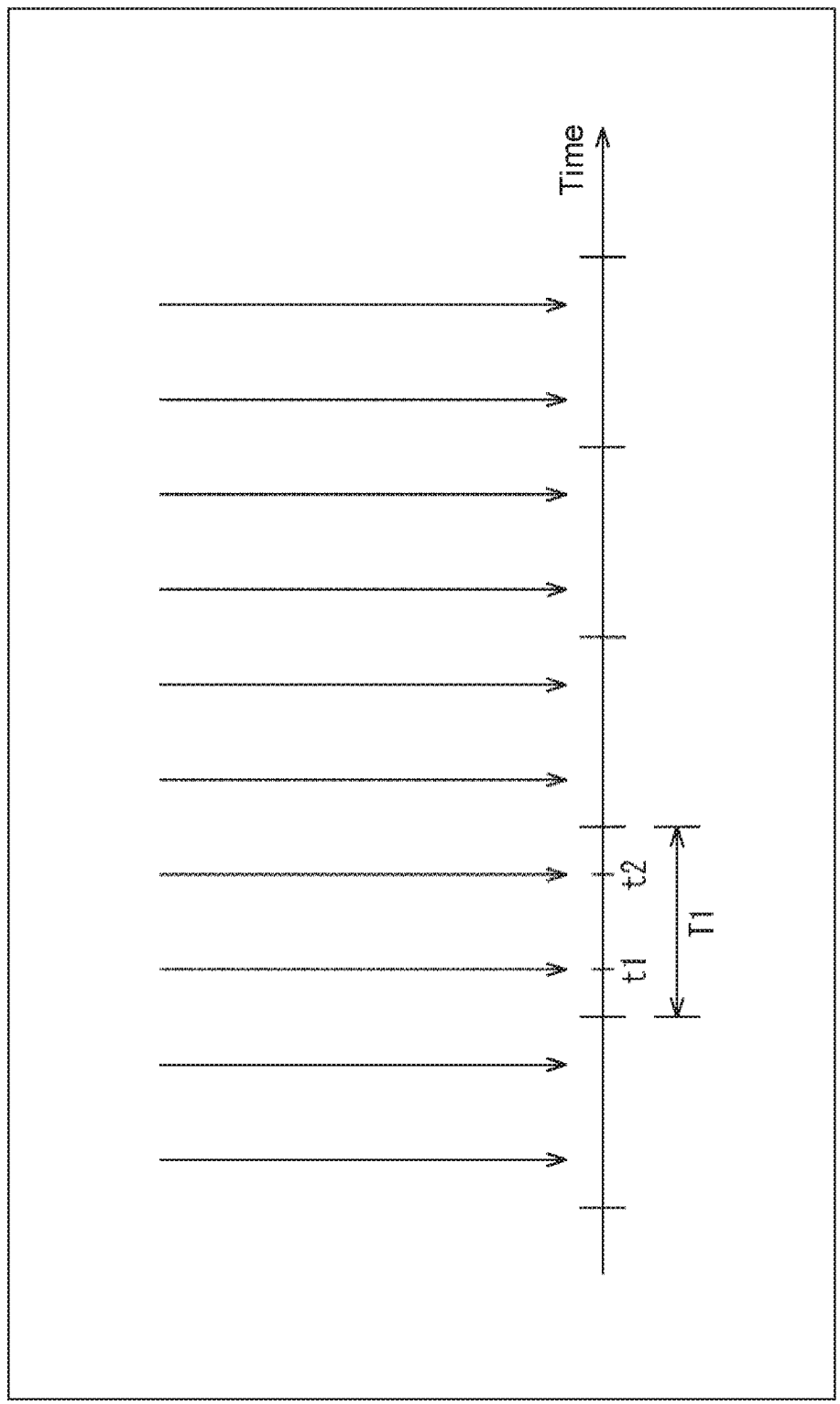
FIG. 3 An explanatory chart showing pulsed-light emissions.

As shown, for example, in FIG. 3, the light source device 23 emits the light beam twice in a time period of one frame corresponding to the input image. Note that, in FIG. 3, the abscissa axis represents time, and downward arrows in FIG. 3 each indicate a timing of the light emission by the light source device 23, that is, a timing of the application of the illumination light beam to the photographic subject.

In this example, for example, a time period T1 represents the time period corresponding to one frame of the input image, that is, an exposure time period for taking the input image corresponding to the one frame. In the time period T1 corresponding to the one frame, the light source device 23 performs the pulsed-light emission at each time point, that is, a time point t1 and a time point t2.

In particular, in this example, at the times of the pulsed-light emissions, light beams containing the same wavelength component, that is, in this example, the white light beams are output from the light source device 23. Further, light-emission control is performed such that the light source device 23 performs the pulsed-light emissions at certain time intervals, that is, in certain periods. The pulsed-light emission by the light source device 23 is performed twice at an equal interval in each of the time periods corresponding to the frames.

For example, when the input images are taken as those of a 60P moving image, the one-frame time period of the input images is $1/60$ s. Thus, the light source device 23 emits the light beams at timings of every $1/120$ s.

In response to the synchronizing signals supplied from the light-source control unit 61, the light source device 23 performs the pulsed-light emissions of the white light beams as the illumination light beams at the intervals of $1/120$ s. When the illumination light beams are applied to the photographic subject, the reflected light beams from the photographic subject enter the imaging unit 62. Thus, the imaging unit 62 performs an imaging operation of receiving and photoelectrically converting the illumination light beams at the timings indicated by the synchronizing signals from the light-source control unit 61.

In this case, for example, the time period T1 is set as the exposure time period, and the imaging unit 62 takes the input image of the frame corresponding to the time period T1. The image data item of the resultant input image is supplied to the motion detection unit 63 and the output-image generation unit 64.

The motion detection unit 63 performs motion detection with respect to the input image supplied from the imaging unit 62, and supplies the resultant motion-information items such as the motion vector to the output-image generation unit 64.

Figure 4:
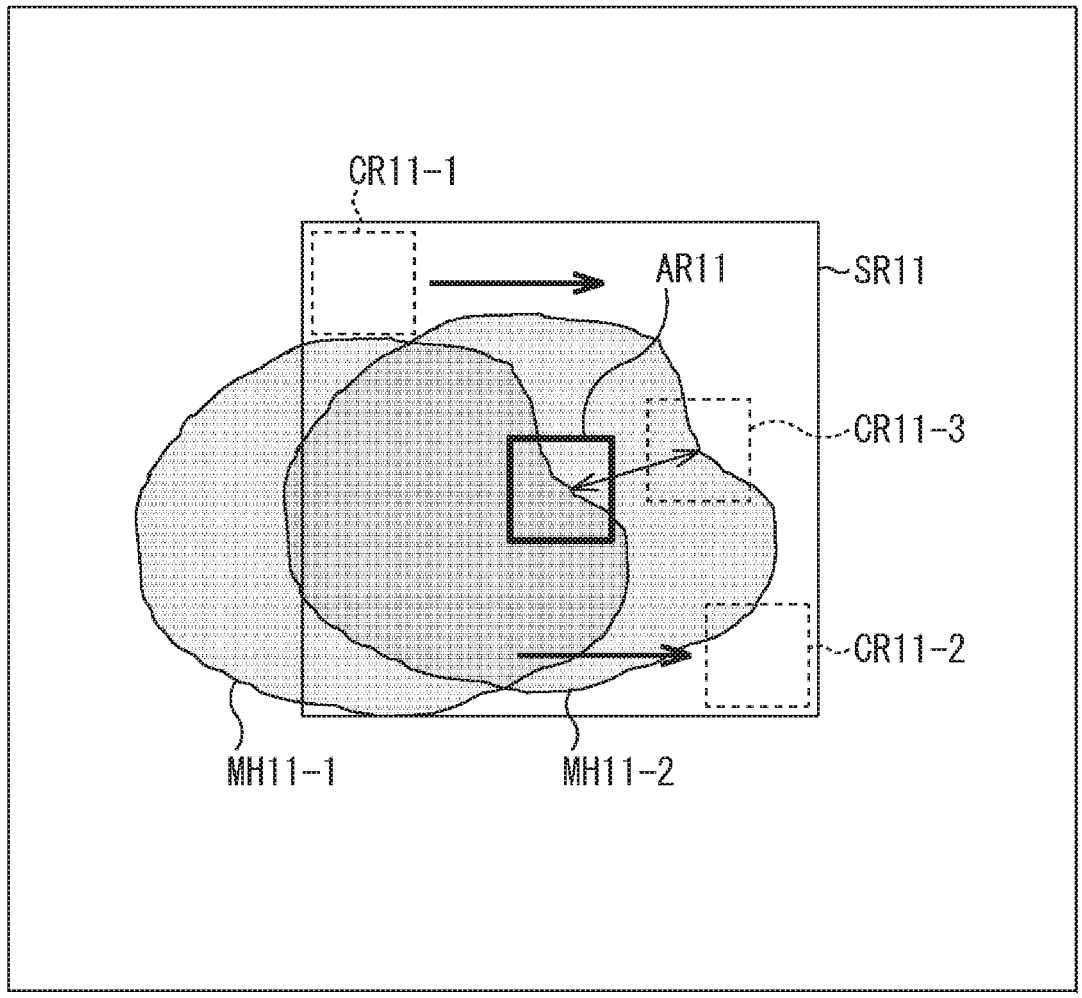
FIG. 4 An explanatory view illustrating motion detection based on an input image.

Specifically, in the case where the illumination light beam is applied twice in the one-frame time period of the input image as shown in FIG. 3, when the input images depict a moving photographic subject, an image of the photographic subject is a double image as illustrated, for example, in FIG. 4.

Note that, when the input images depict the moving photographic subject, the photographic subject itself may be moving, that is, the photographic subject may be an active photographic subject, or the imaging unit 62 may be moving with respect to the photographic subject due to camera shake or the like. In other words, the motion of the photographic subject in the input images obtained as a result of the motion detection with respect to the input images is a motion of the photographic subject itself, a motion of the photographic subject with respect to the imaging unit 62, or both the motions.

In the example of FIG. 4, a photographic-subject image MH11-1 and a photographic-subject image MH11-2 being images of the same photographic subject are contained in the input images. Note that, in the following, unless it is necessary to make a specific distinction between the photographic-subject image MH11-1 and the photographic-subject image MH11-2, these images are simply referred to also as photographic-subject images MH11.

For example, when the input images of FIG. 4 are taken in the time period T1 shown in FIG. 3, one of the two photographic-subject images MH11 is an image corresponding to the reflected light beam that enters the imaging unit 62 at a timing of the time point t1 shown in FIG. 3, and another one of the photographic-subject images MH11 is an image corresponding to the reflected light beam that enter the imaging unit 62 at a timing of the time point t2.

When the light source device 23 performs the pulsed-light emission twice in the exposure time period in this way, the two images of the same photographic subject are contained in the input images. However, which of these two photographic-subject images corresponds to which of the time points cannot be distinguished.

The motion detection unit 63 sets one desired region in an input image corresponding to a processing-target frame as an attention region AR11, and sets a predetermined rectangular region around the attention region AR11 as a search range SR11. In other words, the search range SR11 being a search region is set as a rectangular region corresponding to upper, lower, right, and left detection-target shift ranges with respect to the attention region AR11 in FIG. 4.

The motion detection unit 63 sets regions each having the same size as that of the attention region AR11 at positions in the search range SR11 as comparison regions, and performs search while shifting the comparison regions.

In this example, the search is performed in an order of raster scan from an upper-left comparison region CR11-1 in the search range SR11 in FIG. 4 to a lower-right comparison region CR11-2 in the search range SR11 in FIG. 4. Note that, in the following, unless it is necessary to make specific distinctions between the comparison regions such as the comparison region CR11-1 and the comparison region CR11-2 in the search range SR11, these regions are simply referred to also as comparison regions CR11.

The motion detection unit 63 calculates an autocorrelation coefficient between the attention region AR11 and each of the comparison regions CR11.

Specifically, the motion detection unit 63 calculates an autocorrelation coefficient R from the following equation (1) where a pixel value of an i-th pixel in the attention region AR11 is Xi, and a pixel value of an i-th pixel in the comparison region CR11 is Yi.

[Math. 1]

$$R = \frac{\sum_i (Xi - Xa)(Yi - Ya)}{\sqrt{\sum_i (Xi - Xa)^2} \sqrt{\sum_i (Yi - Ya)^2}} \quad (1)$$

Note that, in the equation (1), Xa is an average value of the pixel values of all pixels in the attention region AR11, and Ya is an average value of the pixel values of all pixels in the comparison region CR11.

When such an autocorrelation coefficient R is calculated with respect to all the comparison regions CR11 in the search range SR11, the autocorrelation coefficient R reaches its maximum value, that is, the autocorrelation coefficient R=1 is obtained when the comparison region CR11 is identical to the attention region AR11.

Further, when the comparison region CR11 corresponds to a second-largest local maximum value of the autocorrelation coefficient R, the comparison region CR11 at this time is a region depicting the same photographic subject as that in the attention region AR11. In other words, the comparison region CR11 at this time is a region shifted from the attention region AR11 by an amount of the motion vector indicating a motion of the photographic subject in the attention region AR11.

In this example, the second-largest local maximum value of the autocorrelation coefficient R is obtained by a combination of the attention region AR11 and the comparison region CR11-3. Thus, an arrow (vector) connecting a center of the attention region AR11 and a center of the comparison region CR11-3 to each other, in other words, displacement between the attention region AR11 and the comparison region CR11-3 corresponds to the motion vector of the attention region AR11.

In this way, the motion detection unit 63 calculates the motion of the photographic subject with respect to the attention region in the input image corresponding to the processing-target frame.

Note that, when the motion is calculated from the images of the same photographic subject contained in the input images, that is, from the double image of the photographic subject, magnitudes of components of a two-dimensional motion vector can be calculated, but directions of the motion vector cannot be calculated.

Figure 5:
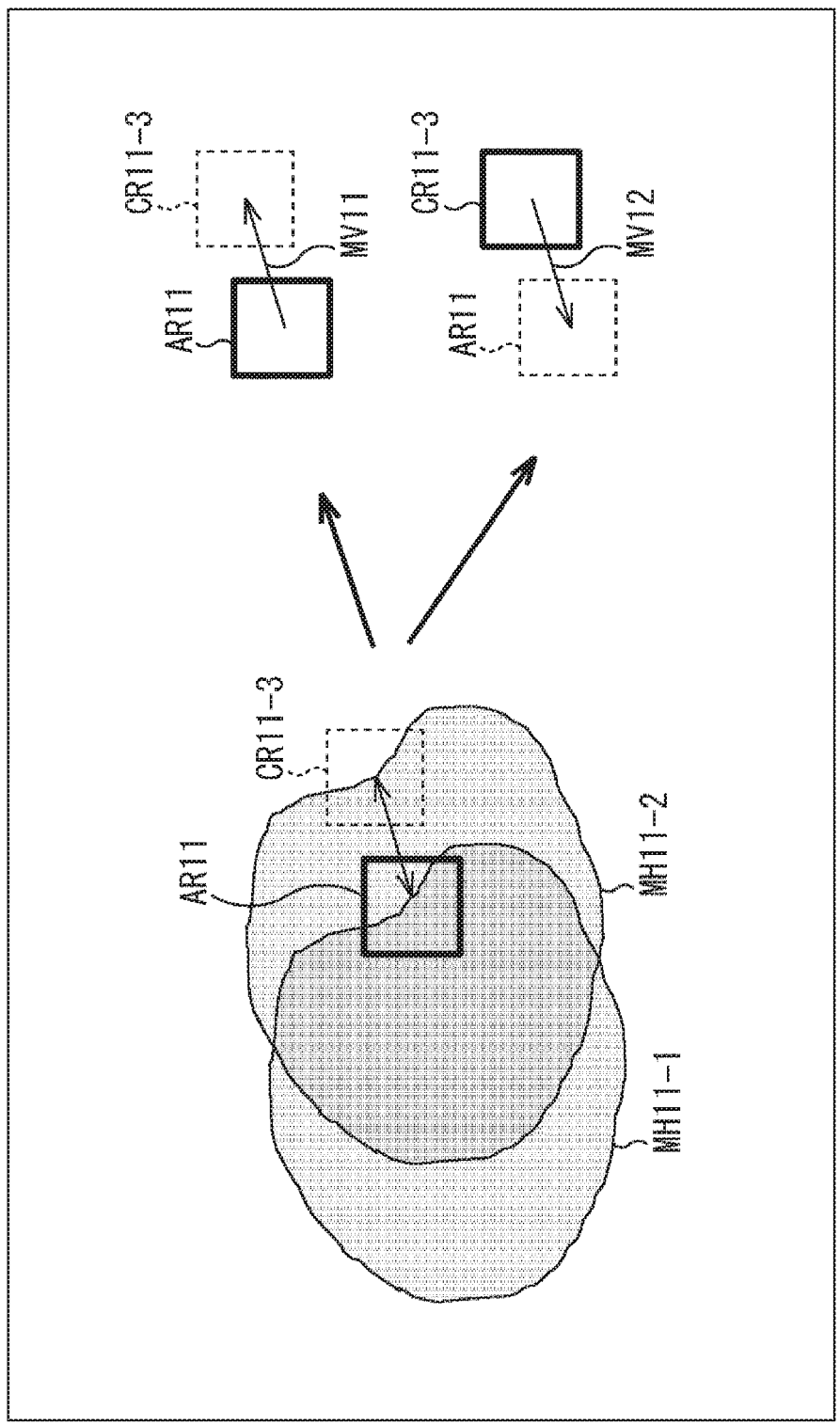
FIG. 5 An explanatory view illustrating directions of a motion.

For example, as illustrated in FIG. 5, with respect to the attention region AR11, the comparison region CR11-3 is calculated as the region corresponding to the second-largest local maximum value of the autocorrelation coefficient R. Note that, in FIG. 5, components corresponding to those in the case of FIG. 4 are denoted by the same reference symbols, and description thereof is omitted as appropriate.

In this case, the vector connecting the attention region AR11 and the comparison region CR11-3 to each other corresponds to the motion vector. However, whether the photographic subject has moved from a position of the attention region AR11 to a position of the comparison region CR11-3 as indicated by an arrow MV11, or the photographic subject has moved from the position of the comparison region CR11-3 to the position of the attention region AR11 as indicated by an arrow MV12 cannot be distinguished from the input image corresponding to one frame.

As a countermeasure, when the direction of the motion is needed as the motion information item, it is only necessary to calculate the direction of the motion with use of input images corresponding to a plurality of frames, specifically, for example, the input image corresponding to the processing-target frame and an input image corresponding to a frame immediately preceding the processing-target frame. In such a case, the direction of the motion can be calculated by utilizing the same method as those at times of detecting general inter-frame motion vectors.

Figure 6:
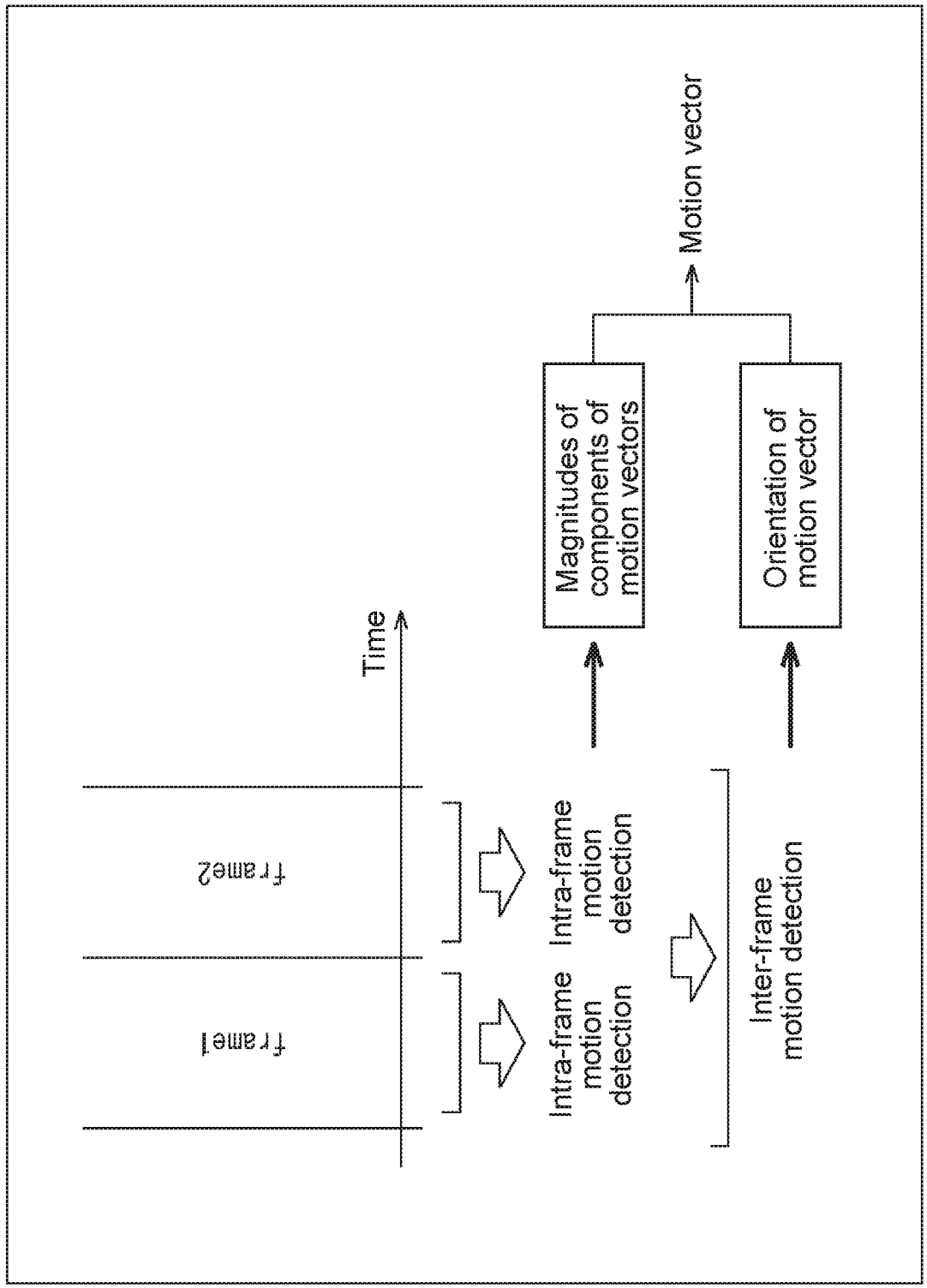
FIG. 6 An explanatory diagram showing generation of a motion information item by the motion detection.

For example, as shown in FIG. 6, it is assumed that there are a frame2 being a frame corresponding to a latest time point, and a frame1 being a frame immediately preceding the frame2.

The motion detection unit 63 performs the motion detection in each of the frame1 and the frame2 so as to calculate a magnitude of a motion vector of the photographic subject in each of input images corresponding to these frames, that is, magnitudes of components in directions such as an x-direction and a y-direction of the motion vector.

With respect to these magnitudes, the motion detection unit 63 performs motion detection such as inter-frame block matching with use of the input images corresponding respectively to the frame1 and the frame2, and determines a direction (orientation) of a resultant motion vector as a direction of a motion of the photographic subject in the latest frame2.

Then, the motion detection unit 63 determines the motion vector that is calculated from the magnitudes of the motion vectors, which are obtained as described above, that is, from the magnitude of the component in each of the directions, and from the direction (orientation) of the motion vector as the motion information item indicating the detected motion.

Normally, when the motion detection is performed with respect to the input images, and the motion correction such as the image stabilization is performed with use of the resultant motion-information item, a motion between the frame1 and the frame2 is detected, and a result of the detection is applied to a frame subsequent to the frame2 (hereinafter, referred to as frame3). However, in this case, an information item of the frame1 that is temporally away from the frame3 is used, and hence the motion detection cannot be performed with high accuracy.

In contrast, in the endoscope system 11, the motion is detected only from the frame2 immediately preceding the frame3 to which the result of the motion detection is applied is detected. Thus, the motion detection is performed with use of an information item newer than that at the time of using the immediately-preceding two frames. For example, at a time of estimating a motion in the frame3, accuracy in motion detection becomes higher by using an information item closer to the frame3. This proves that the motion detection can be performed with higher accuracy at the time of detecting the motion only from the frame2 than at the time of using the immediately-preceding two frames.

Note that, at the time of obtaining the motion vector as the motion information item, also in the endoscope system 11, not only the frame2 but also the preceding frame1 is used for detecting the direction of the motion vector. However, the orientation of the motion vector is scarcely abruptly reversed. Thus, even when the frame1 and the frame2 are used for calculating the direction of the motion vector, accuracy in detection of the resultant motion vector as the motion information item does not decrease.

In the endoscope system 11, the direction (orientation) of the motion vector that scarcely changes is detected with use of the immediately-preceding two frames. Magnitudes of components of the motion vector, which have a significant influence on the detection accuracy, that is, minor motion changes are detected with use of only the latest frame. With this, the motion detection can be performed with higher accuracy.

Note that, although the motion vector with respect to the one attention region in the input image is calculated as the motion information item in the above-described example, the motion vector may be calculated as the motion information item in each of a plurality of regions in an entirety of the input image. Alternatively, one motion vector may be calculated as the motion information item in the entirety of the input image.

Further, although the method of calculating the autocorrelation coefficient is described as an example of methods of calculating the motion vector, the motion vector may be calculated by other matching methods such as a gradient method.

The motion detection unit 63 supplies, as the motion information item, the motion vector calculated as described above to the output-image generation unit 64.

The output-image generation unit 64 generates the output image by performing, for example, the motion correction for correcting a motion amount with respect to the input image with use of the motion information item supplied from the motion detection unit 63, the input image being supplied from the imaging unit 62, the motion amount being calculated from the motion information item. As the motion correction, the image stabilization is performed, for example.

Specifically, the output-image generation unit 64 performs the image stabilization with respect, for example, to the input image on the basis of the motion vector in the processing-target frame, which is estimated from the motion vector as the motion information item obtained from the frame immediately preceding the processing-target frame. In this case, for example, the input image corresponding to the processing-target frame is shifted by an amount of the magnitude of the motion vector into a direction opposite to the orientation of this motion vector, and then is generated as the output image.

Further, alternatively, a correction of the double image contained in the input image may be performed as the motion correction. As described above, in the operation of taking the input image, the pulsed-light emission is performed twice, that is, multiple exposure is performed. Thus, when the photographic subject has moved, two images of the photographic subject are contained in the input image. In this case, the output-image generation unit 64 may execute, on the input image, an image process of removing one of the two images of the same photographic subject with use of the motion information item, the two images being contained in the input images, and then output another one of the two images as the output image.

The output-image generation unit 64 supplies the output image generated in this way to the recorder 65, and causes the recorder 65 to record this output image. The output-image generation unit 64 also supplies this output image to the monitor 26, and causes the monitor 26 to display this output image.

As described above, in the endoscope system 11, the magnitudes of the components of the motion vector as the motion information item can be calculated from the input image corresponding to the latest one frame, that is, from one input image. With this, the motion detection of the photographic subject in the input image can be performed with higher accuracy.

Further, in the endoscope system 11, the calculated motion information item can be immediately utilized for the motion correction process on the subsequent frame. Thus, the output image can be obtained while reducing a delay to a minimum.

In addition, as another example, the output-image generation unit 64 may detect a time point (frame) when the photographic subject does not make the motion from the motion information item of the attention region, which is obtained by the motion detection unit 63, and then generate an output image being an image for observing the photographic subject from an input image taken at the time point when the photographic subject does not make the motion. Alternatively, when a state in which the photographic subject does not make the motion is detected, the signal processing circuit 32 may control the imaging unit 62 such that the imaging unit 62 immediately takes a new input image, for example, by a normal light emission under the state in which the photographic subject has not moved, and that the output image for the observation is generated from the obtained input image.

In these cases, the image of the photographic subject is not doubled in the input image. Thus, the motion correction is unnecessary, and an unblurred still image can be obtained as the output image.

The time point when the motion is not made, for example, a time point when the motion vector as the motion information item is zero or substantially zero. Such a time point is, for example, a time point when there is no comparison region corresponding to the second-largest local maximum value of the autocorrelation coefficient, or a time point when the second-largest local maximum value of the autocorrelation coefficient is equal to or less than a predetermined threshold.

Further, when the output image under the state in which the photographic subject does not make the motion is to be obtained, it is only necessary to grasp only presence/absence of the motion, and hence the direction of the motion is unnecessary. Therefore, in such a case, only the magnitudes of the components of the motion vector may be detected as the motion information item.

The method of generating the output image by detecting the time point at which the motion is not made is particularly advantageous, for example, at a time of acquiring the diagnostic unblurred still image.

The endoscope system 11 as described above is particularly advantages, for example, at the time of executing the image stabilization process, or at the time of acquiring a motionless still image.

When the motion of the photographic subject is dynamic, accuracy in normal motion detection of the dynamic motion decreases due to motion blurring. However, in the endoscope system 11, the pulsed-light emissions are performed at the time of the exposure. Thus, blurring of the input image to be acquired can be reduced, and the motion detection can be performed with high accuracy even with respect to rapid motions. Further, when the pulsed-light emissions are performed, a substantial exposure time period is shortened. Thus, even motions that rapidly change, and vibrating motions in short periods also can be detected with high accuracy.

<Imaging Procedure>

Figure 7:
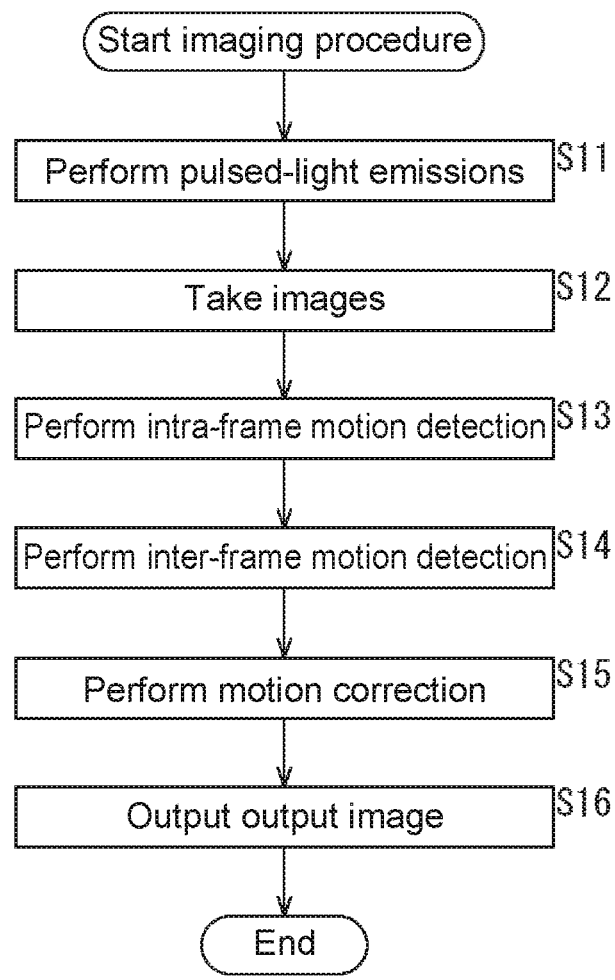
FIG. 7 An explanatory flowchart showing an imaging procedure.

Next, with reference to a flowchart of FIG. 7, a procedure in which the endoscope system 11 generates the output images is described. In other words, in the following, with reference to the flowchart of FIG. 7, an imaging procedure by the endoscope system 11 is described.

In Step S11, the light source device 23 performs the pulsed-light emissions under control by the light-source control unit 61. Specifically, the light source device 23 performs the pulsed-light emission twice per frame time period at the timings indicated by the synchronizing signals from the light-source control unit 61.

In Step S12, the imaging unit 62 takes the input images in response to the synchronizing signals supplied from the light-source control unit 61.

Specifically, the imaging unit 62 obtains the input images by receiving and photoelectrically converting the incident reflected-light beams. In this example, the pulsed-light emission is performed twice per frame time period, that is, per exposure time period. Thus, the input images are each a multiple-exposure image containing the images of the photographic subject at the times of the respective pulsed-light emissions. The imaging unit 62 supplies the obtained input images to the motion detection unit 63 and the output-image generation unit 64.

In Step S13, the motion detection unit 63 performs the intra-frame motion detection on the basis of each of two of the input images supplied from the imaging unit 62 and each corresponding to one frame.

Specifically, the motion detection unit 63 detects the comparison region corresponding to the second-largest local maximum value by performing the calculation using the above-described equation (1) with respect to the attention region in one of the two of the input images. In this way, the motion detection unit 63 calculates the magnitudes of the components of the motion vector in the processing-target frame.

In Step S14, the motion detection unit 63 performs the inter-frame motion detection on the basis of the input image corresponding to the processing-target frame and the input image corresponding to the frame immediately preceding the processing-target frame.

Specifically, the motion detection unit 63 detects the direction (orientation) of the motion vector by performing, for example, the block matching on the basis of the input images corresponding to the immediately-preceding two frames. Note that, the present technology is not limited to the example described hereinabove in which the direction of the motion vector as the motion of the photographic subject in the input images is detected with use of the input images corresponding to the immediately-preceding two frames. However, the direction of the motion vector may be detected with use of a plurality of different frames, that is, input images at a plurality of different time points.

By the processes of these Step S13 and Step S14, the motion vector in the processing-target frame is obtained. The motion detection unit 63 supplies, as the motion information item, the motion vector obtained in this way to the output-image generation unit 64.

Note that, more specifically, the processes of Step S13 and Step S14 are executed simultaneously, that is, concurrently with each other.

In Step S15, the output-image generation unit 64 performs, on the basis of the motion information item supplied from the motion detection unit 63, the motion correction with respect to the input image supplied from the imaging unit 62, and then generates the output image.

For example, in Step S15, the image stabilization process on the input image corresponding to the processing-target frame is executed as the motion correction on the basis of the motion information item obtained from the frame immediately preceding the processing-target frame, and then the output image is generated. In this case, the motion information item calculated in Step S13 and Step S14 is used in a subsequent frame. Thus, the process of Step S15 may be executed simultaneously with the processes of these Step S13 and Step S14. Alternatively, the process of Step S15 may be executed before the execution of the processes of Step S13 and Step S14. Note that, when real-time characteristics are not required, the motion correction with respect to the input image corresponding to the processing-target frame may be performed with use of a motion information item obtained from this processing-target frame.

In Step S16, the output-image generation unit 64 outputs the output image obtained by the process of Step S15 to the recorder 65 or the monitor 26. Then, the imaging procedure is ended. With this, the output image is recorded in the recorder 65, or the output image is displayed on the monitor 26.

As described above, by performing the pulsed-light emissions a plurality of times in one-frame time period, the endoscope system 11 detects a motion, specifically, the magnitudes of the components of the motion vector from the input image corresponding to one frame. With this, the motion detection can be performed with higher accuracy and with a small delay.

Second Embodiment

<Motion Detection>

Further, in the example described in the first embodiment, the laser light source that emits the RGB white-light beams is used as the light source device 23. However, the light source device 23 may be, for example, a laser light source capable of sequentially performing pulsed-light emissions of laser light beams respectively containing color components of R, G, and B.

Figure 8:
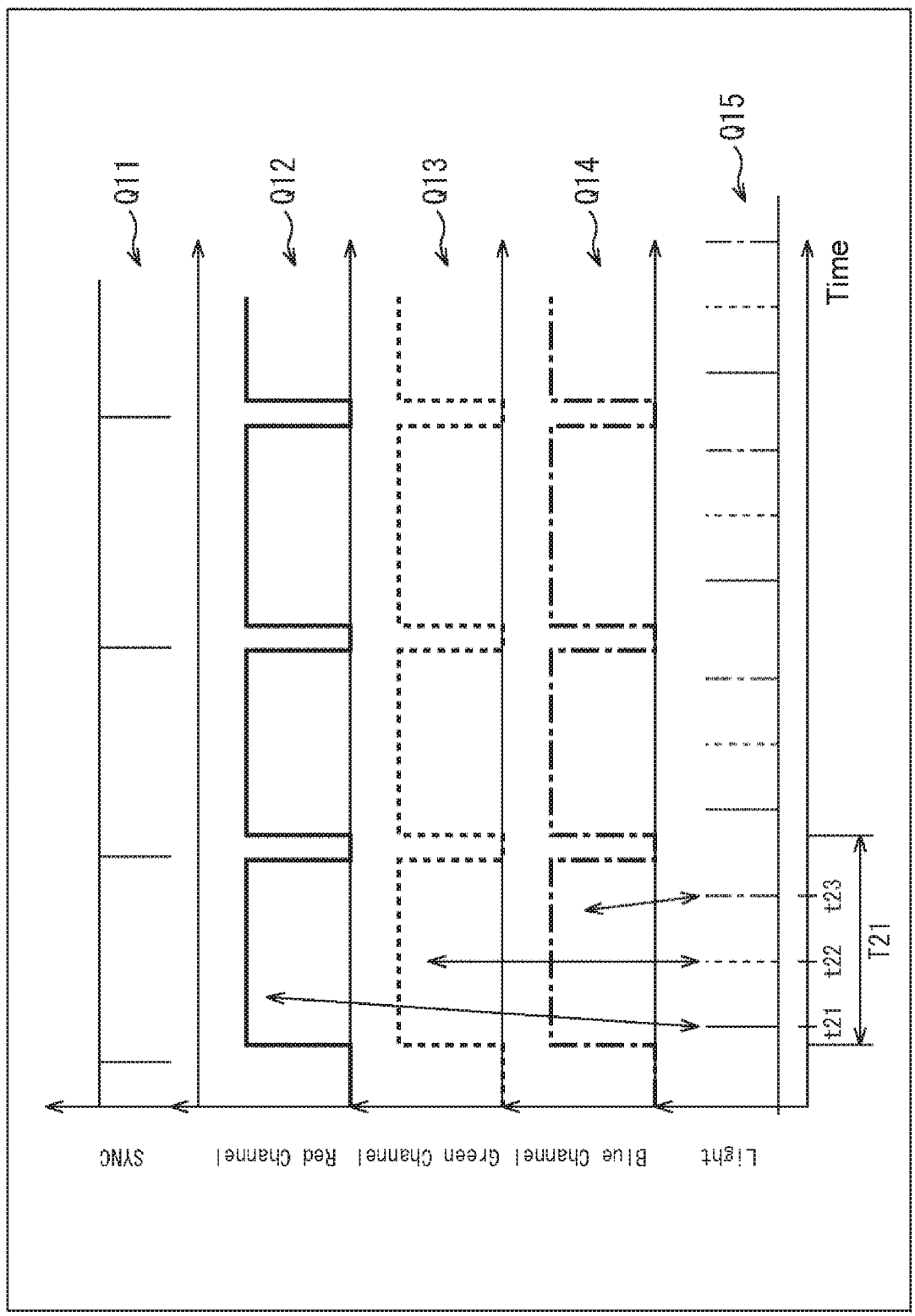
FIG. 8 An explanatory chart showing pulsed-light emissions in respective colors in one-frame time period.

In such a case, as shown in FIG. 8, the light source device 23 sequentially performs the pulsed-light emissions of the light beams respectively containing the color components of R (Red), G (Green), and B (Blue), for example, once each in a time period corresponding to one frame. In other words, the light-source control unit 61 performs light-emission control such that, respectively at times of the plurality of times of pulsed-light emissions in the time period corresponding to one frame, the light beams containing the color components different from each other, that is, light beams containing wavelength components different from each other are output from the light source device 23. Note that, in FIG. 8, the abscissa axis represents time.

In this embodiment, the light source device 23, which includes the "R" light source, the "G" light source, and the "B" light source, causes these light sources to sequentially and independently perform the pulsed-light emissions. With this, the light beam containing the "R" component, the light beam containing the "G" component, and the light beam containing the "B" component can be sequentially emitted as the illumination light beams.

In FIG. 8, a section indicated by an arrow Q11 corresponds to the synchronizing signals for the frames corresponding to the input images. Specifically, in FIG. 8, in the section indicated by the arrow Q11, concave-upward parts correspond to boundary positions between the frames.

Further, sections indicated respectively by an arrow Q12 to an arrow Q14 correspond respectively to exposure timings of the light beams containing the "R" components, the light beams containing the "G" components, and the light beams containing the "B" components. For example, in FIG. 8, in the section indicated by the arrow Q12, concave-downward time periods each correspond to one-frame exposure time period of the light beam containing the "R" component. In particular, in this example, irrespective of the frames, the light beams containing the "R" components, the light beams containing the "G" components, and the light beams containing the "B" components are exposed at their respective common timings.

In addition, a section indicated by an arrow Q15 corresponds to light emission timings of the pulsed-light emissions by the light source device 23. Specifically, solid-line parts each correspond to a light emission timing of the light beam containing the "R" component from the "R" right source, dotted-line parts each correspond to a light emission timing of the light beam containing the "G" component from the "G" right source, and dash-dotted-line parts each correspond to a light emission timing of the light beam containing the "B" component from the "B" right source.

In this example, a time period T21 corresponds, for example, to the time period of one frame corresponding to the input image, and the pulsed-light emission is performed three times in this time period T21. Specifically, first, at a time point t21, the light beam of the "R" color, that is, the illumination light beam containing the "R" component is output by the pulsed-light emission. Then, at a time point t22, the illumination light beam containing the "G" component is output by the pulsed-light emission. Next, at a time point t23, the illumination light beam containing the "B" component is output by the pulsed-light emission.

For example, when the input images are taken as those of the 60P moving image, the one-frame time period of the input images is 1/60 s. Thus, the light source device 23 emits the light beams in an order of R, G, and B at timings of every 1/180 s. Specifically, focusing on the color components of the light beams, the light beams of the same color are emitted at the timings of every 1/60 s.

Further, in the imaging unit 62, exposure is performed at appropriate timings in accordance with the light emission timings of the light source device 23. When the imaging unit 62 is, for example, a Bayer-array single-plate sensor, on an imaging surface of the imaging unit 62, color filters that transmit therethrough only the light beams respectively containing the color components of R, G, and B are provided respectively to the pixels. Specifically, on the imaging surface of the imaging unit 62, "R" pixels that receive only the light beams containing the "R" components, "G" pixels that receive only the light beams containing the "G" components, and "B" pixels that receive only the light beams containing the "B" components are provided.

In the example of FIG. 8, all the color components are exposed at their respective common timings, and an image to be obtained by the exposure corresponding to one frame is an image of what is called a RAW data item including the "R" pixels, the "G" pixels, and the "B" pixels (hereinafter, referred to as RAW image).

Thus, when the "R" pixels are extracted from the RAW image, and an interpolation process and the like are executed thereon as appropriate, an "R" image formed only of the "R" pixels, that is, having values of only the "R" components is obtained. Similarly, when the "G" pixels are extracted from the RAW image, and the interpolation process and the like are executed thereon as appropriate, a "G" image formed only of the "G" pixels is obtained. When the "B" pixels are extracted from the RAW image, and the interpolation process and the like are executed thereon as appropriate, a "B" image formed only of the "B" pixels is obtained.

In other words, by taking the RAW image, the "R" image is obtained from "R" signals being pixel signals output from the "R" pixels, the "G" image is obtained from "G" signals being pixel signals output from the "G" pixels, and the "B" image is obtained from "B" signals being pixel signals output from the "B" pixels. In still other words, by executing a demosaic process on one RAW image, plain images respectively containing the color components of R, G, and B, that is, the "R" image, the "G" image, and the "B" image are obtained from the RAW image.

When the imaging unit 62 includes the pixels of the color components, although the light emission timings of the light beams respectively containing the color components are different from each other, the exposure time periods of the color components can be set equal to each other, specifically, to the time period corresponding to one frame. In other words, by performing the pulsed-light emissions at timings different from each other correspondingly respectively to the color components in the one-frame time period, the plain images that respectively containing the color components and images at the time points different from each other can be obtained from the taken RAW image corresponding to one frame.

Note that, although, in FIG. 8, for the sake of simplicity of description, description is made by way of an example in which global shutter imaging, that is, all the pixels in the imaging unit 62 are exposed at once, the "R" image, the "G" image, and the "B" image can be obtained in the same way also when rolling shutter imaging, that is, exposures and readout are performed in each pixel row.

Substantial imaging time points of the plain images respectively containing the three color components, which are obtained from the RAW image corresponding to one frame in this way, are shifted from each other by a time period of ⅓ frames. Thus, the motion detection unit 63 performs the intra-frame motion detection with use of these "R" image, "G" image, and "B" image in the same frame so as to detect the motion of the photographic subject in the attention region.

Figure 9:
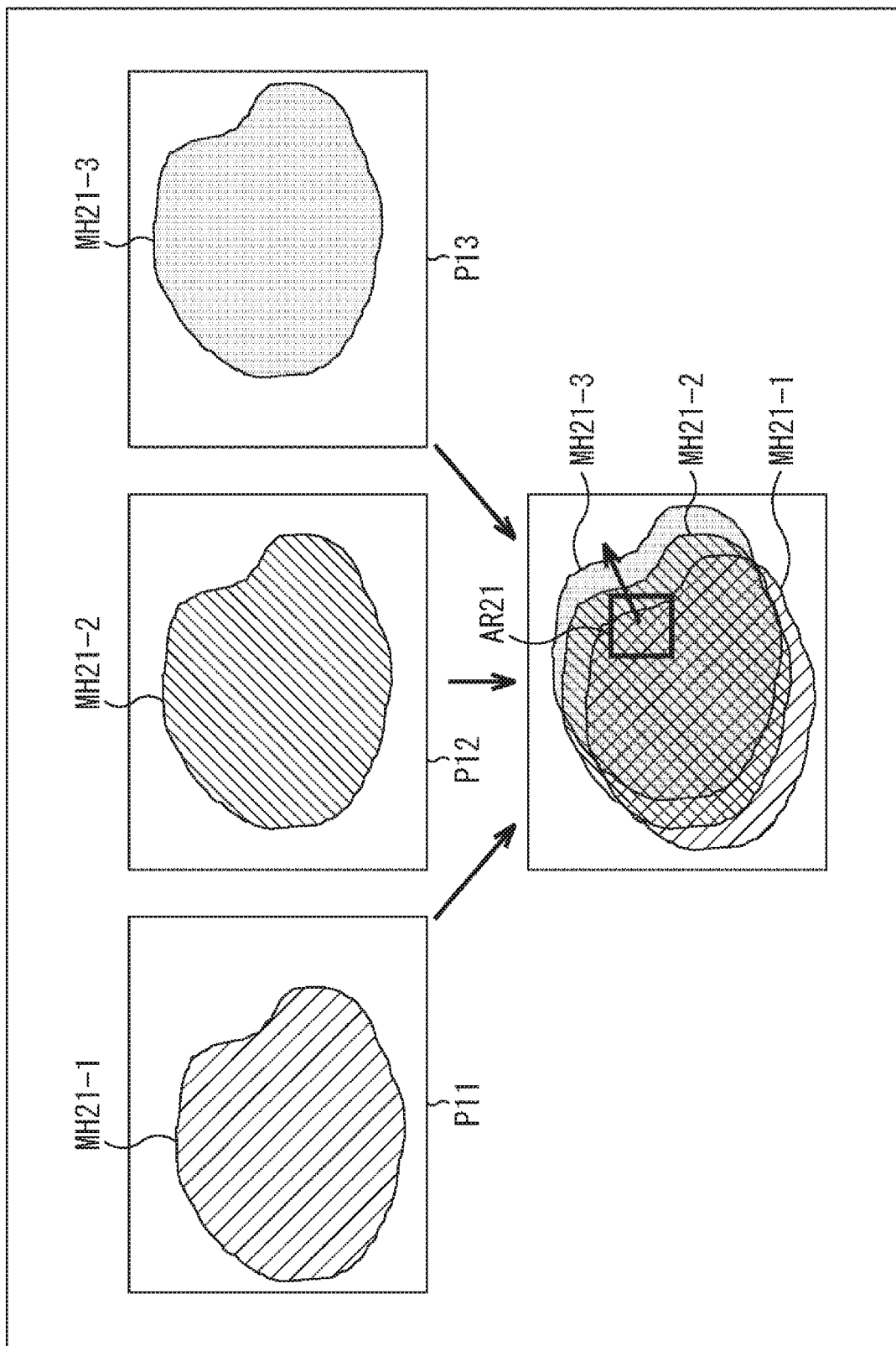
FIG. 9 An explanatory view illustrating motion detection with use of plain images.

In this case, as illustrated in FIG. 9, for example, three plain images, that is, an "R" image P11, a "G" image P12, and a "B" image P13 are obtained by imaging in the time period corresponding to one frame.

In this example, a photographic-subject image MH21-1 is observed in the "R" image P11, a photographic-subject image MH21-2 is observed in the "G" image P12, and a photographic-subject image MH21-3 is observed in the "B" image P13. These photographic-subject image MH21-1 to photographic-subject image MH21-3 are images of the same photographic subject at the different time points. Note that, in the following, unless it is necessary to make specific distinctions between the photographic-subject image MH21-1 to the photographic-subject image MH21-3, these images are simply referred to also as photographic-subject images MH21.

The "R" image P11 to the "B" image P13 are the images at the time points different from each other. Thus, when these images are superimposed on each other, as illustrated, for example, in a lower part of FIG. 9, it is apparent that the photographic-subject images MH21 observed in the images are slightly shifted from each other.

The motion detection unit 63 calculates a motion vector of an attention region AR21 with use of the "R" image P11 to the "B" image P13 and by, for example, a general motion-detection technique.

Specifically, the motion detection unit 63 detects, for example, a comparison region from each of the "G" image P12 and the "B" image P13, the comparison region corresponding to a maximum of an autocorrelation coefficient with respect to the desired attention region AR21 in the "R" image P11.

Then, the motion detection unit 63 calculates the motion vector of the photographic subject in the attention region AR21 from a positional relationship between the attention region AR21 in the "R" image P11, the comparison region in the "G" image P12, which corresponds to the maximum of the autocorrelation coefficient, and the comparison region in the "B" image P13, which corresponds to the maximum of the autocorrelation coefficient.

Note that, in this example, an order relationship between the time points of the photographic-subject images contained respectively in the "R" image P11 to the "B" image P13 has been already grasped. Thus, not only magnitudes of components of the motion vector, but also a direction of the motion can be obtained. Thus, the motion vector can be calculated only from an information item of one frame.

<Another Imaging Procedure>

Figure 10:
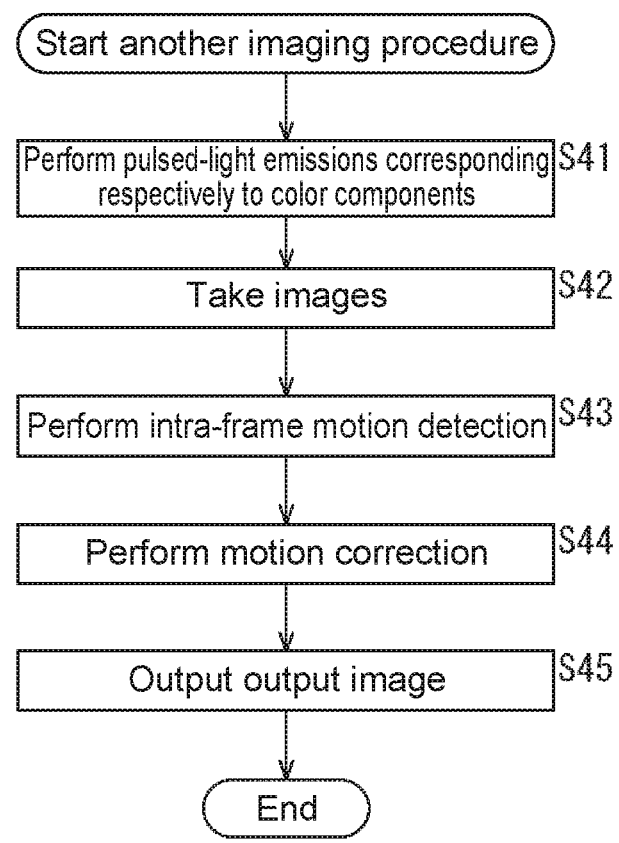
FIG. 10 An explanatory flowchart showing another imaging procedure.

Next, a procedure that is executed in the endoscope system 11 at the time when the pulsed-light emissions of the light beams respectively containing the color components of R, G, and B are sequentially performed is described. In other words, in the following, with reference to the flowchart of FIG. 10, another imaging procedure by the endoscope system 11 is described.

In Step S41, the light source device 23 performs the pulsed-light emissions corresponding respectively to the color components of R, G, and B under the control by the light-source control unit 61.

Specifically, the light source device 23 performs the pulsed-light emission three times in total per frame time period, specifically, once for each of the colors of R, G, and B in this order at the timings indicated by the synchronizing signals from the light-source control unit 61.

In Step S42, the imaging unit 62 takes the input images in response to the synchronizing signals supplied from the light-source control unit 61. Specifically, the imaging unit 62 takes the RAW images as the input images by receiving and photoelectrically converting the incident reflected-light beams. Then, the imaging unit 62 obtains, on the basis of each of the RAW images, the "R" image formed only of the "R" pixels, the "G" image formed only of the "G" pixels, and the "B" image formed only of the "B" pixels as the plain images. Next, the imaging unit 62 supplies the plain images respectively containing these color components as final input images to the motion detection unit 63 and the output-image generation unit 64. Note that, the RAW images may be output as the input images such that, for example, in the output-image generation unit 64 in a subsequent stage, the plain images respectively containing the color components are generated from the RAW images.

In Step S43, the motion detection unit 63 calculates the motion vector by performing the intra-frame motion detection on the basis of each of the input images supplied from the imaging unit 62 and each corresponding to one frame, specifically, on the basis of the "R" image, the "G" image, and the "B" image corresponding to one frame. Then, the motion detection unit 63 supplies the motion vector as the motion information item to the output-image generation unit 64.

After the motion information item is obtained, processes of Step S44 and Step S45 are executed, and then the imaging procedure is ended. These processes are the same as the processes of Step S15 and Step S16 in FIG. 7, and hence description thereof is omitted.

Note that, in Step S44, for example, the image stabilization process is executed as the motion correction on each of the plain images respectively containing the color components as the input images. By synthesizing the plain images respectively containing the color components after the image stabilization, a color output image including the pixels of the color components of R, G, and B is generated.

As described above, the endoscope system 11 performs the pulsed-light emissions at the timings different from each other correspondingly respectively to the plurality of colors in one-frame time period, detects the motion from the input image corresponding to one frame, and generates the output image with use of the result of the detection. With this, the motion detection can be performed with higher accuracy and with a small delay.

Third Embodiment

<Motion Detection>

Incidentally, in the above-described example, the motion of the photographic subject is detected from the input images for generating the observational output images. However, images to be used for the motion detection (hereinafter, referred to also as detection images) may be generated independently of the input images for generating the output images. More specifically, the input images and the detection images may be generated as images at different time points of the same moving image.

Figure 11:
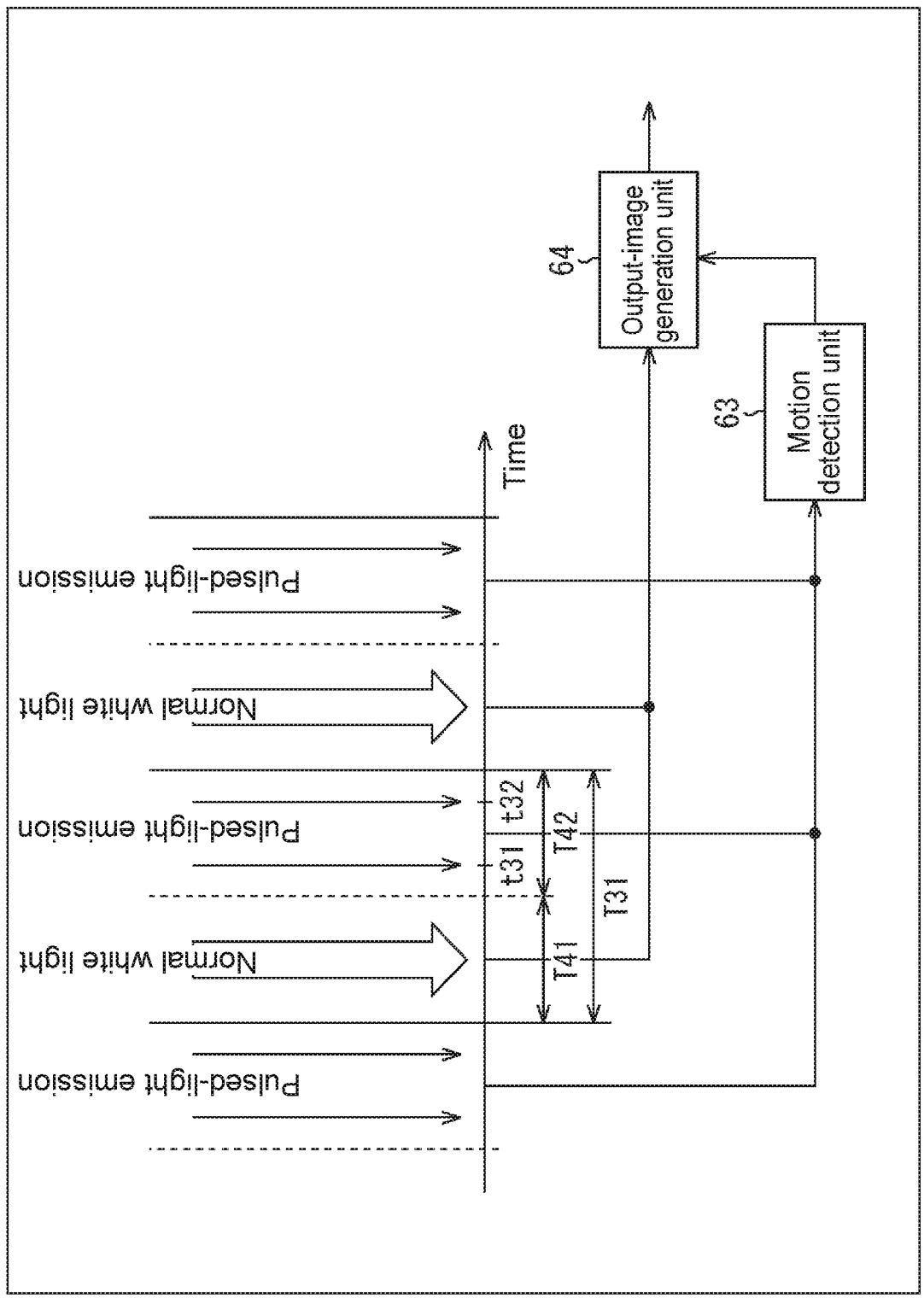
FIG. 11 An explanatory chart showing a normal light emission and pulsed-light emissions in one-frame time period.

In such a case, as shown in FIG. 11, it is only necessary, for example, to sequentially separate a time period for the motion detection, that is, a field for the detection image, and a time period for the normal light, that is, a field for the input image from each other.

Note that, in FIG. 11, components corresponding to those in the case of FIG. 2 are denoted by the same reference symbols, and description thereof is omitted as appropriate. Further, in FIG. 11, the abscissa axis represents time, and downward arrows in FIG. 11 indicate timings of the light emissions by the light source device 23.

In the example shown in FIG. 11, a time period of one frame corresponding to the input image (output image) is divided into the two sequential fields. Specifically, a time period T31 is, for example, the time period of one frame corresponding to the input image, and this time period T31 is divided into two time periods, specifically, a time period T41 and a time period T42.

Here, the time period T41 is set as a time period corresponding to one field for obtaining the input image, that is, a time period for exposing the input image. During the time period T41, the light source device 23 performs a normal light emission of the white light beam. In other words, during the time period T41, the light source device 23 continues to apply the white light beam to the photographic subject.

In this example, as in the first embodiment, the light source device 23 is the laser light source that emits the white light beams. However, a light source for emitting the illumination light beam at the time of the normal light emission, and a light source for performing the pulsed-light emissions of the illumination light beams for the motion detection may be provided independently of each other.

For example, when the input images are taken by causing the light source device 23 to perform the pulsed-light emissions, light intensity during the exposure time period is lower than that at a time when the white light beam is continuously emitted. Thus, brightness may be insufficient for observing the photographic subject in the input image.

As a countermeasure, in the example shown in FIG. 11, the time period T41 that is half of the time period T31 of one frame corresponding to the input image is set as the time period of one field. During this time period of one field, the white light beam is continuously output from the light source device 23. In addition, the time period T41 is set as the time period for exposing the input image.

Further, the time period T42 subsequent to the time period T41 is set as a time period of another one field in which, as in the first embodiment, the light source device 23 is caused to perform the pulsed-light emission twice. Specifically, in the time period T42, first, at a time point t31, the light source device 23 is caused to perform the pulsed-light emission such that the white light beam is applied to the photographic subject. Then, at a time point t32, the light source device 23 is caused to perform the pulsed-light emission again such that the white light beam is applied to the photographic subject.

The time period T42 corresponding to the other one field in which the pulsed-light emission is performed twice in this way is set not as the exposure time period of the input image, but as an exposure time period of the detection image for detecting the motion of the photographic subject (attention region).

Thus, for example, when a frame rate of the output images is 60 fps, a length of the time period T31 corresponding to one frame is set to 1/60 s, and the time period T41 and the time period T42 are each set to 1/120 s.

From another perspective, in this example, a first exposure time period in which a light beam containing a predetermined wavelength component, that is, the white light beam is continuously output, and a second exposure time period in which the pulsed-light emission of the white light beam is performed a plurality of times are provided in the time period corresponding to one frame. Thus, it can be said that two images are taken in this time period corresponding to one frame. In addition, the image obtained in the first exposure time period is used as the input image for generating the output image, and the image obtained in the second exposure time period is used as the detection image for detecting the motion.

Note that, although the one-frame time period is divided into the two fields in the example described in this embodiment, the time period for obtaining the input image, and the time period for obtaining the detection image may each be set as one-frame time period, and these time periods may be provided alternately to each other.

In this case, among the plurality of frames constituting the taken moving image, frames each corresponding the first exposure time period in which the white light beam is continuously output are used as the input images, and frames each corresponding to the second exposure time period in which the pulsed-light emission of the white light beam is performed a plurality of times are used as the detection images.

In the example shown in FIG. 11, light-emission control and imaging control are performed such that time periods each corresponding to one frame, which is constituted by the time period corresponding to one field for obtaining the input image and by the subsequent time period corresponding to the other one field for obtaining the detection image, are arranged in series in a time direction. In other words, the light-emission control and the imaging control are performed such that the fields for obtaining the input images and the fields for obtaining the detection images are arranged alternately to each other.

In this case, in the fields in each of which the normal light emission is performed, the images taken by the imaging unit 62 are supplied as the input images to the output-image generation unit 64. In contrast, in the fields in each of which the pulsed-light emissions are performed, the images taken by the imaging unit 62 are supplied as the detection images to the motion detection unit 63.

Then, in the motion detection unit 63, the motion vector is calculated as in the case of the first embodiment from the supplied detection images, and the obtained motion vector is supplied as the motion information item to the output-image generation unit 64.

Further, in the output-image generation unit 64, on the basis of the motion information item supplied from the motion detection unit 63, the motion correction such as the image stabilization process are performed as appropriate with respect to the input images supplied from the imaging unit 62. In this way, the output images are generated.

<Still Another Imaging Procedure>

Figure 12:
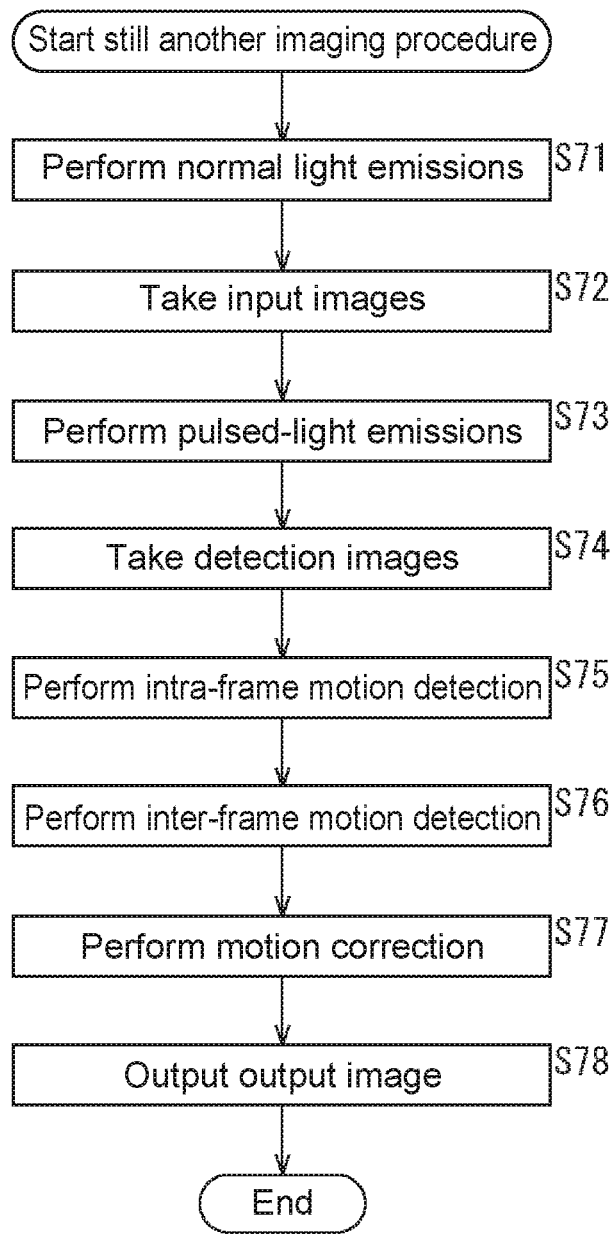
FIG. 12 An explanatory flowchart showing still another imaging procedure.

Next, a procedure that is executed in the endoscope system 11 at the time when the one-frame time period is divided into the field for obtaining the input image and the field for obtaining the detection image is described. In other words, in the following, with reference to the flowchart of FIG. 12, still another imaging procedure by the endoscope system 11 is described.

In Step S71, the light source device 23 performs the normal light emissions under the control by the light-source control unit 61. Specifically, the light source device 23 continuously emits and applies the white light beam to the photographic subject during the time period corresponding to one frame at the timing indicated by the synchronizing signal from the light-source control unit 61.

In Step S72, the imaging unit 62 takes the input images in response to the synchronizing signals supplied from the light-source control unit 61, and supplies the obtained input images to the output-image generation unit 64.

In Step S73, the light source device 23 performs the pulsed-light emissions under the control by the light-source control unit 61. Specifically, in Step S73, the process similar to that of Step S11 in FIG. 7 is executed, more specifically, the pulsed-light emission is performed twice in the one-field time period.

In Step S74, the imaging unit 62 takes the detection images in response to the synchronizing signals supplied from the light-source control unit 61.

Specifically, the imaging unit 62 obtains each of the detection images by receiving and photoelectrically converting the incident reflected-light beams in the exposure time period being an entirety or a part of the one-field time period in which the pulsed-light emissions are performed. In this example, the pulsed-light emission is performed twice per field time period. Thus, the detection images are each the multiple-exposure image containing the images of the photographic subject at the times of the respective pulsed-light emissions. The imaging unit 62 supplies the obtained detection images to the motion detection unit 63.

After corresponding one of the input images and corresponding one of the detection images are obtained in the time period corresponding to one frame in this way, processes of Step S75 to Step S78 are executed, and then the imaging procedure is ended. These processes are the same as the processes of Step S13 to Step S16 in FIG. 7, and hence description thereof is omitted.

Note that, in Step S75 and Step S76, the intra-frame motion detection and the inter-frame motion detection are performed on the basis of the detection images so as to obtain the motion information item. Further, the processes of Step S75 and Step S76 are executed concurrently with each other. In addition, in Step S77, the motion correction is performed with respect to the input image, and then the output image is generated.

As described above, the endoscope system 11 performs the normal light emission in the time period corresponding to the one field being first half of one-frame time period so as to obtain the input image, and performs the pulsed-light emissions in the time period corresponding to the other one field being second half of the one-frame time period so as to obtain the detection image. Then, the endoscope system 11 detects the motion from the detection image, and generates the output image with use of the result of the detection and the input image. With this, the motion detection can be performed with higher accuracy and with a small delay.

Fourth Embodiment

<Motion Detection>

Further, when the time period in which the normal light emission is performed to obtain the input image, and the time period in which the pulsed-light emissions are performed to obtain the detection image are separated from each other, the normal light emission may be basically performed, and the pulsed-light emissions may be temporarily performed when necessary.

Figure 13:
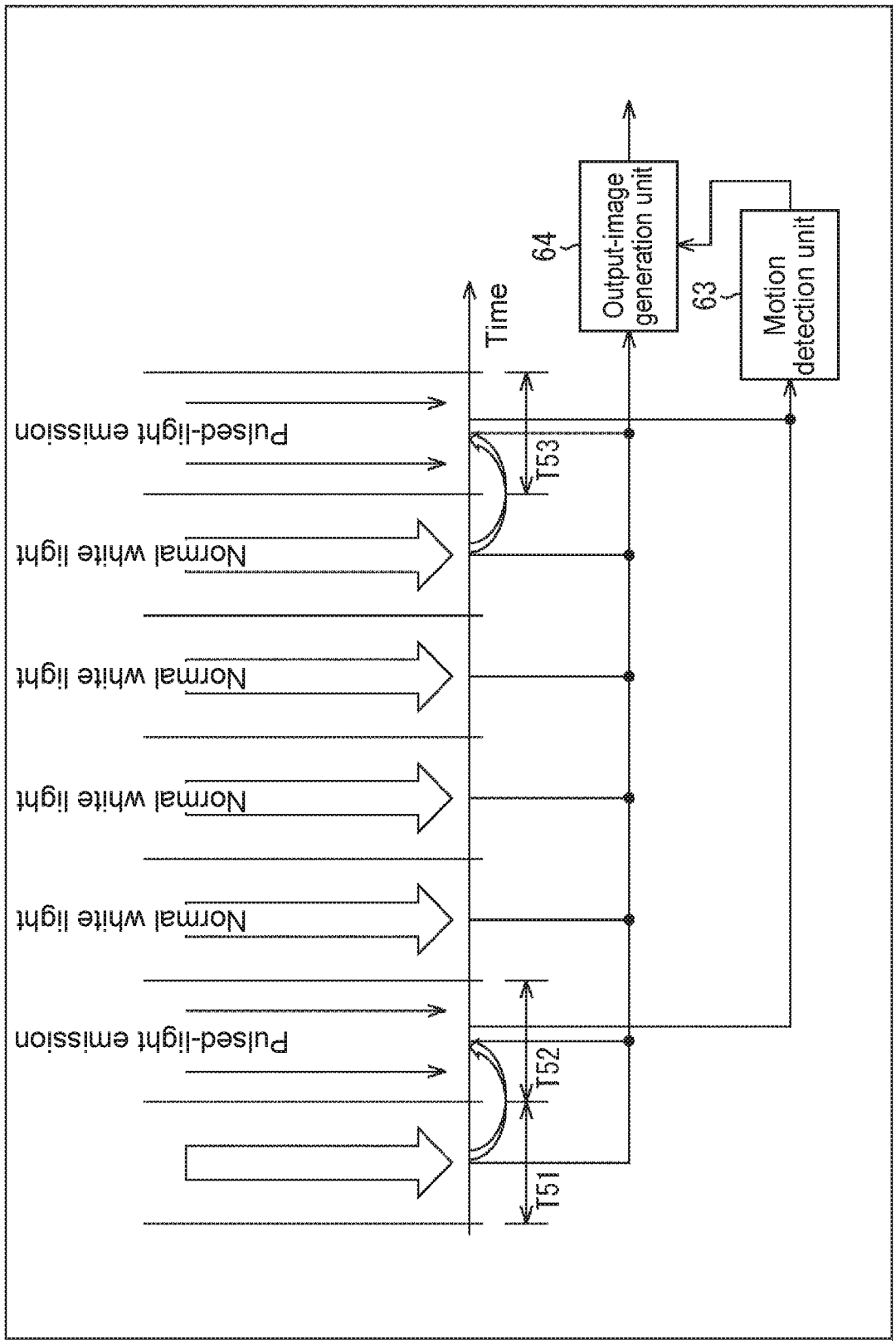
FIG. 13 Another explanatory chart showing the normal light emissions and the pulsed-light emissions.

In such a case, as shown in FIG. 13, for example, whether to perform the normal light emission or to perform the pulsed-light emissions may be switched on a frame-by-frame basis. In frames in each of which the pulsed-light emissions are performed, the input images may be obtained by the interpolation process. Note that, in FIG. 13, components corresponding to those in the case of FIG. 2 are denoted by the same reference symbols, and description thereof is omitted as appropriate. Further, in FIG. 13, the abscissa axis represents time, and downward arrows in FIG. 13 indicate timings of the light emissions by the light source device 23.

In the example shown in FIG. 13, the first exposure time periods in each of which the white light beam is continuously output, and the second exposure time periods in each of which the pulsed-light emission of the white light beam is performed a plurality of times are provided. Then, among the plurality of frames constituting the taken moving image, images of frames corresponding to the first exposure time periods are used as the input images, and images of frames corresponding to the second exposure time periods are used as the detection images.

In this way, in the endoscope system 11, ones of the frames of the taken moving image are used as the input images, and other ones of the frames are used as the detection images. In the following, a sentence "input images and detection images are taken on a frame-by-frame basis" is also used.

In FIG. 13, in a time period T51 corresponding to a predetermined one frame, as, for example, in the time period T41 in FIG. 11, the light source device 23 continuously emits the white light beam (performs the normal light emission). This time period T51 is set as the time period for exposing the input image. In other words, when the time period T51 has elapsed, the input image corresponding to one frame is obtained.

Further, in a time period T52 subsequent to the time period T51 and corresponding to one frame, as in the time period T42 in FIG. 11, the light source device 23 performs the pulsed-light emission twice so as to take the detection image. In other words, the time period T52 is set as the exposure time period in which the pulsed-light emission is performed twice, and an image corresponding to one frame, which is obtained in this time period T52, is used as the detection image.

Respectively in four time periods subsequent to the time period T52, each of which corresponds to one frame, the light source device 23 perform the normal light emissions of the white light beams so as to take the input images corresponding respectively to the frames. In a time period T53 subsequent thereto and corresponding to one frame, as in the time period T52, the light source device 23 performs the pulsed-light emission twice so as to take the detection image.

In this way, in the example shown in FIG. 13, between the frames in each of which the normal light emission is performed, the frames in each of which the pulsed-light emissions are performed are partially inserted. Note that, intervals of the frames (exposure time periods) in each of which the pulsed-light emissions are performed, the intervals being partially inserted between the frames in each of which the normal light emission is performed, may be equal or may be unequal.

For example, when frames in each of which the pulsed-light emission is performed a plurality of times are arranged at unequal intervals, the signal processing circuit 32 may control the imaging unit 62 and the light-source control unit 61 in response, for example, to operation inputs by a user such that the frames in each of which the pulsed-light emissions are performed can be inserted at arbitrary timings. In other words, the signal processing circuit 32 may be capable of switching whether to take the input images or to take the detection images at the arbitrary timings.

In such a case, as, for example, in the time period T51, in the frame in which the normal light emission is performed, the output-image generation unit 64 generates the output image from the taken input image corresponding to one frame.

Further, as, for example, in the time period T52, in the frame in which the pulsed-light emissions are performed, the motion detection unit 63 calculates, as the motion information item, the motion vector from the detection image by the same method as that in the first embodiment. At the time of calculating the direction of the motion, there may be used, for example, a detection image corresponding to closest one of previous frames in each of which the pulsed-light emissions are performed, the closest one being closest to a processing-target frame in which the pulsed-light emissions are performed. Alternatively, there may be used an input image corresponding to an adjacent frame in which the normal light emission is performed, the adjacent frame being temporally adjacent to the processing-target frame in which the pulsed-light emissions are performed.

Further, as, for example, in the time period T52, in the frame in which the pulsed-light emissions are performed, the input image is not obtained. Thus, in this frame, the input image is generated by the interpolation process including motion compensation that is performed at least from an input image corresponding to an immediately-preceding frame, and from the motion information item.

Specifically, the output-image generation unit 64 performs, for example, the motion compensation with respect to the input image of the frame corresponding to the time period T51 with use of the motion information item obtained in the frame corresponding to the time period T52, which is supplied from the motion detection unit 63. With this, the output-image generation unit 64 generates an input image of the frame corresponding to the time period T52.

Note that, the input image of the frame corresponding to the time period T52 may be generated with use of input images of the plurality of adjacent frames that are preceding and subsequent to this frame. For example, the input image of the frame corresponding to the time period T52 may generated by executing the interpolation process, specifically, by performing the motion compensation with use of the motion information item and from the input image of the frame corresponding to the time period T51, and the input image of the frame immediately subsequent to the frame corresponding to the time period T52.

Further, when the motion compensation is performed with respect to the input images corresponding to the frames, a motion information item of corresponding one of the frames, or a motion information item of closest one of the previous frames, which is closest to the corresponding one of the frames, is used.

<Yet Another Imaging Procedure>

Figure 14:
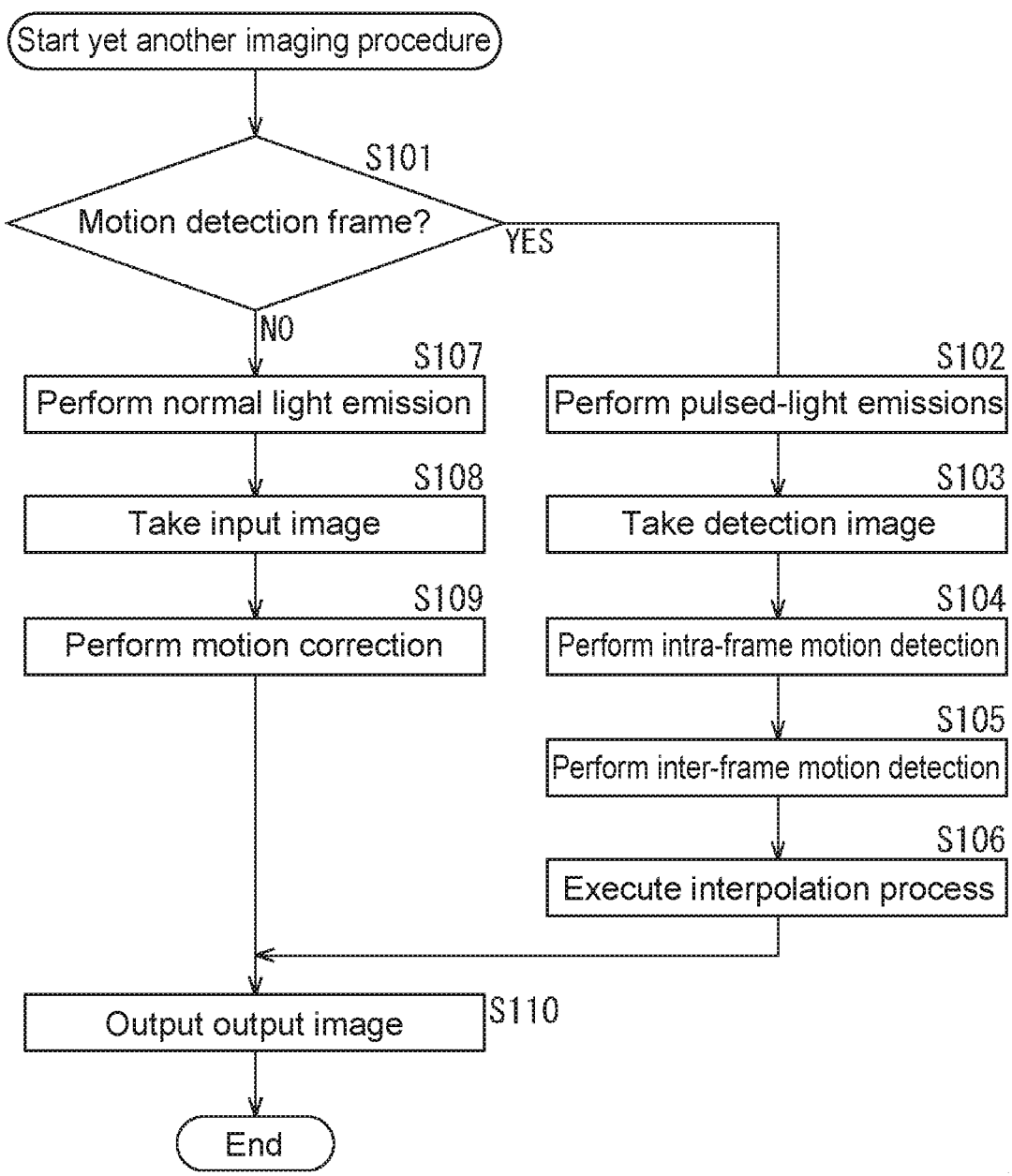
FIG. 14 An explanatory flowchart showing yet another imaging procedure.

Next, a procedure that is executed in the endoscope system 11 at the time when the frames in each of which the pulsed-light emissions are performed are inserted as appropriate between the frames in each of which the normal light emission is performed is described. In other words, in the following, with reference to the flowchart of FIG. 14, yet another imaging procedure by the endoscope system 11 is described.

In Step S101, the light-source control unit 61 determines whether or not a processing-target current frame is a motion detection frame, that is, whether or not the processing-target current frame is the frame in which the pulsed-light emissions are performed.

In Step S101, when the processing-target current frame is determined to be the motion detection frame, the procedure proceeds to Step S102. Then, processes of Step S102 to Step S105 are executed. With this, the detection image is taken, and the motion information item is generated. Note that, the processes of these Step S102 to Step S105 are the same as the processes of Step S73 to Step S76 in FIG. 12, and hence description thereof is omitted.

In Step S106, the output-image generation unit 64 executes the interpolation process on the basis of the motion information item obtained from the processing-target current frame in Step S105, and of the input image supplied from the imaging unit 62. With this, the output-image generation unit 64 generates, as the output image, the input image corresponding to the processing-target current frame.

In the interpolation process, for example, at least the input image corresponding to a frame immediately preceding the current frame is used. After the output image is obtained in this way, the procedure proceeds to Step S110.

Further, in Step S101, when the processing-target current frame is determined not to be the motion detection frame, that is, determined to be the frame in which the normal light emission is performed, the procedure proceed to Step S107.

Then, processes of Step S107 to Step S109 are executed, and the output image corresponding to the processing-target current frame is generated. Note that, the processes of these Step S107 to Step S109 are the same as the processes of Step S71, Step S72, and Step S77 in FIG. 12, and hence description thereof is omitted.

Note that, in Step S109, the motion correction is performed with use of a motion information item obtained from temporally closest one of the frames preceding the processing-target current frame, in each of which the pulsed-light emissions are performed, that is, with use of the motion information item obtained most lately by the process of Step S105.

After the output image is obtained by performing the motion correction in Step S109, the procedure proceeds to Step S110.

When the output image is obtained by executing the process of Step S109 or Step S106, in Step S110, the output-image generation unit 64 outputs the obtained output image to the recorder 65 or the monitor 26. Then, the imaging procedure is ended. With this, the output image is recorded in the recorder 65, or the output image is displayed on the monitor 26.

As described above, the endoscope system 11 performs the normal light emission in each of the normal frames so as to obtain the input images, and performs the pulsed-light emissions in each of the frames inserted as appropriate so as to obtain the detection images. Then, the endoscope system 11 detects the motion from the detection images, and generates the output image with use of the result of the detection and the input images. With this, the motion detection can be performed with higher accuracy and with a small delay.

Fifth Embodiment

<Motion Detection>

Note that, although whether to perform the normal light emissions or to perform the pulsed-light emissions is switched on the frame-by-frame basis or the field-by-field basis in the embodiments described hereinabove, when, for example, the light beams to be output by the normal light emissions, and the light beams to be output by the pulsed-light emissions have different wavelength components, these light beams can be emitted together.

Figure 15:
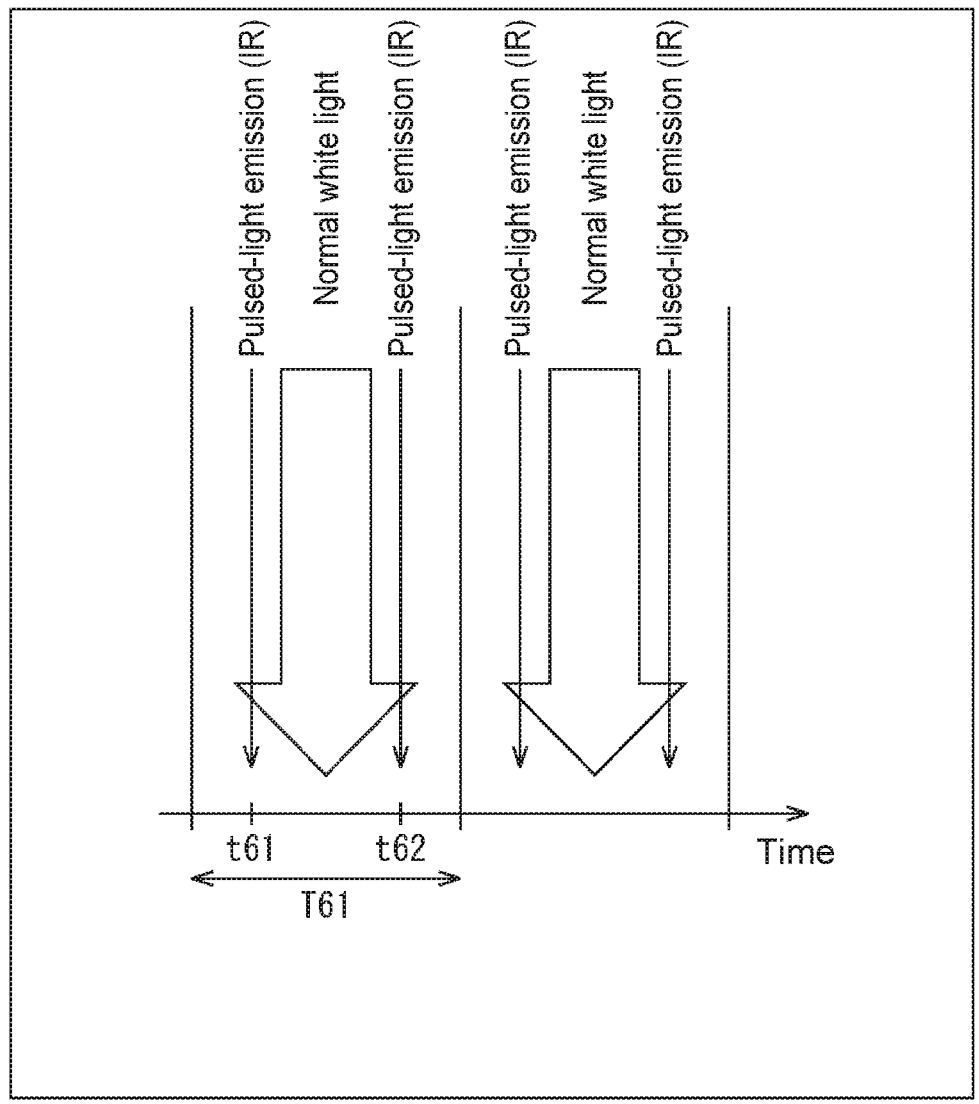
FIG. 15 An explanatory chart showing the normal light emission and pulsed-light emissions in one-frame time period.

Specifically, as shown in FIG. 15, for example, in the time period corresponding to each of the frames, the normal light emission can be continuously performed, and the pulsed-light emission can be performed twice per frame. Note that, in FIG. 15, the abscissa axis represents time, and downward arrows in FIG. 15 indicate timings of the light emissions by the light source device 23.

In this case, for example, the light source device 23 includes the laser light source that performs the normal light emissions so as to output the white light beams as the illumination light beams, that is, the RGB laser-light source constituted by the "R" light source, the "G" light source, and the "B" light source. The light source device 23 also includes an infrared-laser light source that performs the pulsed-light emissions so as to output infrared rays for the motion detection.

The infrared-laser light source is a laser light source capable of pulsed-light emissions of, for example, infrared rays having a wavelength of 850 nm. Further, infrared components are not contained in the white light beams as the illumination light beams. The laser light source that outputs such white light beams is not limited to the RGB laser-light source, and may be other light sources such as a xenon light source and an LED light source.

In the example shown in FIG. 15, for example, a time period T61 is a time period of one frame corresponding to the input image and the detection image. During this time period T61, the normal light emission of the white light beam is continuously performed. Further, in the time period T61, the pulsed-light emission of the infrared ray is also performed twice. In this example, the pulsed-light emissions are performed respectively at two time points, that is, a time point t61 and a time point t62. With this, the infrared rays are applied to the photographic subject.

When the normal light emission of the white light beam and the pulsed-light emissions of the infrared rays are performed in one-frame time period in this way, on the imaging unit 62 side, that is, on the camera head 22 side, an optical system that splits these white light beam and infrared rays from each other, and sensors (imaging units) that respectively receive the white light beam and the infrared rays are needed.

Figure 16:
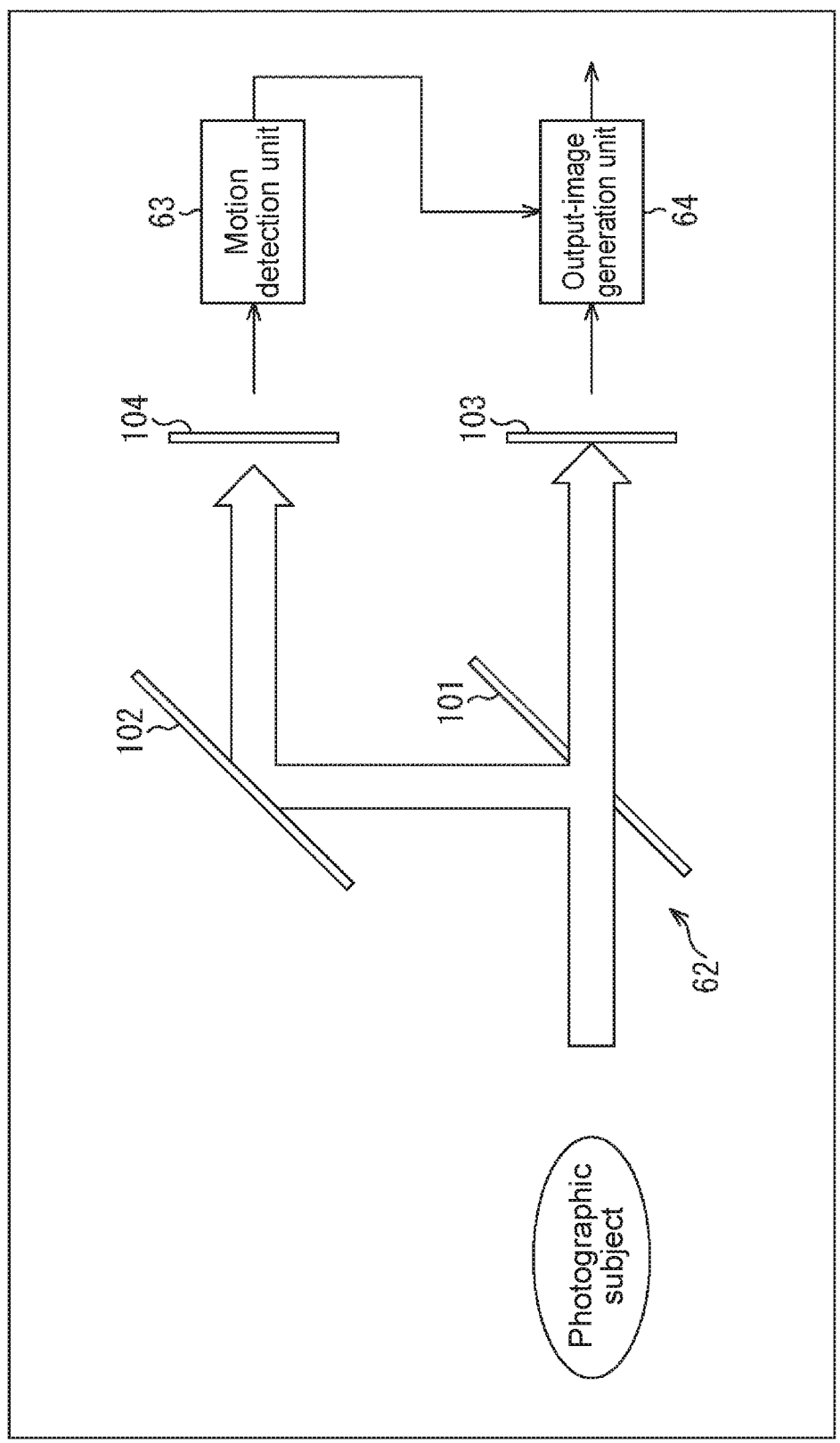
FIG. 16 A diagram showing a configuration example of an imaging unit.

Thus, when the normal light emission of the white light beam and the pulsed-light emissions of the infrared rays are performed in the one-frame time period, more specifically, the imaging unit 62 is configured, for example, as shown in FIG. 16. Note that, in FIG. 16, components corresponding to those in the case of FIG. 2 are denoted by the same reference symbols, and description thereof is omitted as appropriate.

In the example shown in FIG. 16, the imaging unit 62 includes a splitting element 101, a mirror 102, a visible-light sensor 103, and an infrared sensor 104.

In this example, in the time period corresponding to each of the frames, the reflected light beam of the white light beam by the normal light emission, and reflected rays of the infrared rays by the pulsed-light emissions from the photographic subject enter the splitting element 101.

The splitting element 101, which is constituted, for example, by a prism, a dichroic mirror, or a half mirror, optically splits the incident reflected-light beams from the photographic subject. Further, the mirror 102, which is constituted, for example, by a total reflection mirror, reflects and inputs the incident light beams from the splitting element 101 to the infrared sensor 104.

The visible-light sensor 103, which is constituted by an image sensor including a plurality of pixels that receive and photoelectrically convert visible light beams, takes the input images by receiving and photoelectrically converting the incident white light beams from the splitting element 101, and supplies the obtained input images to the output-image generation unit 64. This visible-light sensor 103 functions as the imaging unit that takes the input images for obtaining the observational output images.

The pixels of the visible-light sensor 103 are each provided with an infrared cut filter that blocks the infrared rays. With this, visible-light components of the light beams that have entered the visible-light sensor 103, that is, only the components of the white light beams are received by photodiodes of the pixels.

Further, the infrared sensor 104, which is constituted by an image sensor including a plurality of pixels that receives and photoelectrically converts the infrared rays, takes the detection images by receiving and photoelectrically converting the incident infrared rays from the mirror 102, and supplies the obtained detection images to the motion detection unit 63. This infrared sensor 104 functions as the imaging unit that takes the detection images to be used for the motion detection.

The pixels of the infrared sensor 104 are each provided with a visible-light cut filter that blocks the visible light beams. With this, only the components of the infrared rays among the light beams that have entered the infrared sensor 104 are received by photodiodes of the pixels.

For example, when the splitting element 101 is constituted by the prism or the dichroic mirror, the splitting element 101 transmits and inputs, to the visible-light sensor 103, the components of the white light beams among the incident reflected-light beams from the photographic subject, that is, the visible-light components. In addition, the splitting element 101 reflects the components of the infrared rays among the incident reflected-light beams from the photographic subject. Then, the infrared rays, which are reflected by the splitting element 101 and enter the mirror 102, are reflected by the mirror 102, and then enter the infrared sensor 104.

With this, visible-light input images are obtained by the visible-light sensor 103, and infrared detection images are obtained by the infrared sensor 104.

Further, when the splitting element 101 is constituted by the half mirror, the splitting element 101 transmits and inputs, to the visible-light sensor 103, ones of the incident light beams from the photographic subject. In addition, the splitting element 101 reflects rest of the light beams, that is, other ones of the incident light beams. At this time, the rest of the light beams, which is reflected by the splitting element 101 and enter the mirror 102, is reflected by the mirror 102, and then enter the infrared sensor 104.

In this case, the ones of the light beams, which enter the visible-light sensor 103, include the white-light components and the infrared components. However, the infrared rays are blocked by the infrared cut filter provided to each of the pixels of the visible-light sensor 103, and only the white light beams are received by the visible-light sensor 103. With this, the visible-light input images are obtained by the visible-light sensor 103.

Further, the other ones of the light beams, which enter the infrared sensor 104, also include the white-light components and the infrared components. However, the visible light beams are blocked by the visible-light cut filter provided to each of the pixels of the infrared sensor 104, and only the infrared rays are received by the infrared sensor 104. With this, the infrared detection images are obtained by the infrared sensor 104.

<Yet Another Imaging Procedure>

Figure 17:
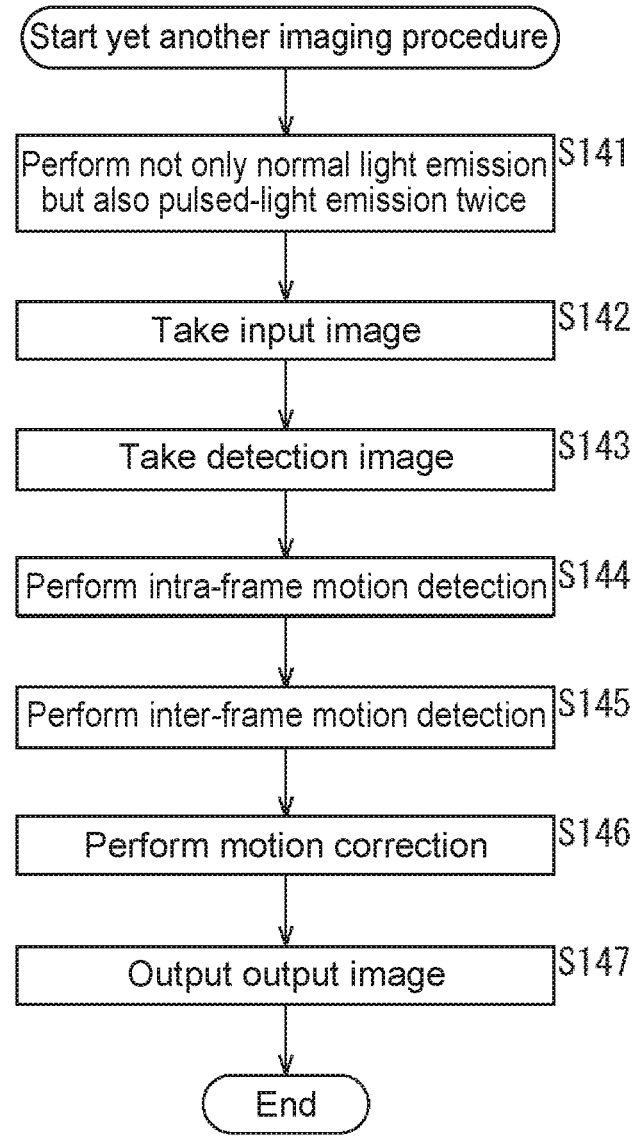
FIG. 17 An explanatory flowchart showing yet another imaging procedure.

Next, a procedure that is executed in the endoscope system 11 at the time when the normal light emission and the pulsed-light emissions are performed in one-frame time period is described. In other words, in the following, with reference to the flowchart of FIG. 17, yet another imaging procedure by the endoscope system 11 is described.

In Step S141, the light source device 23 performs not only the normal light emission so as to continuously apply the white light beam as the illumination light beam to the photographic subject during the one-frame time period, but also the pulsed-light emission twice at predetermined timings in the one-frame time period so as to apply the infrared rays to the photographic subject.

Specifically, the light-source control unit 61 controls the RGB-laser light source as the light source device 23 such that the RGB-laser light source continuously outputs the white light beam during the exposure time period of the input image. In addition, the light-source control unit 61 controls the infrared-laser light source as the light source device 23 such that the infrared-laser light source outputs the infrared rays each having the wavelength different from that of the white light beam by performing the pulsed-light emission twice during the exposure time period of the detection image. In this procedure, the exposure time period of the input image and the exposure time period of the detection image are basically the same time period. However, there is no particular problem as long as the exposure time period of the detection image, that is, the time period in which the pulsed-light emission is performed twice includes at least a part of the exposure time period of the input image, in which the normal light emission by the RGB-laser light source is performed.

By such light-emission control, at each of the time points in the one-frame time period, only the white light beam or both the white light beam and the infrared ray are applied to the photographic subject. The reflected light beams generated by the application of the white light beam and the infrared rays to the photographic subject enter the splitting element 101 of the imaging unit 62. For example, the white light beam among the reflected light beams transmits through the splitting element 101, and then enters the visible-light sensor 103. Further, the infrared rays among the reflected light beams are reflected by the splitting element 101 and the mirror 102, and then enter the infrared sensor 104.

In Step S142, the visible-light sensor 103 of the imaging unit 62 takes the input image by receiving and photoelectrically converting the incident white light beam, and supplies the obtained input image to the output-image generation unit 64.

In Step S143, the infrared sensor 104 of the imaging unit 62 takes the detection image by receiving and photoelectrically converting the infrared rays, and supplies the obtained detection image to the motion detection unit 63. Note that, the processes of these Step S142 and Step S143 are executed simultaneously with each other.

After the input image and the detection image are obtained, processes of Step S144 to Step S147 are executed, and then the imaging procedure is ended. These processes are the same as the processes of Step S75 to Step S78 in FIG. 12, and hence description thereof is omitted. Note that, the processes of Step S144 and Step S145 are executed concurrently with each other, and that the motion correction that is performed with respect to the input image in Step S146 is on the basis of the motion information item obtained from the detection image.

As described above, the endoscope system 11 performs the normal light emission and the pulsed-light emissions together in one-frame time period so as to obtain the input image and the detection image. Then, the endoscope system 11 detects the motion from the detection image, and generates the output image with use of the result of the detection and the input image. With this, the motion detection can be performed with higher accuracy and with a small delay.

Sixth Embodiment

<Another Functional Configuration Example of Endoscope System>

Incidentally, the endoscope system 11 to which the present technology is applied is advantageous also at a time of performing vocal-cord observation.

Generally, vocal cords vibrate at a frequency of several hundred Hz, and hence still images of the vocal cord parts cannot be acquired by normal observation. In view of such circumstances, there has been devised laryngo-stroboscopy including applying illumination light beams from a stroboscopic light source in accordance with vibration periods of the vocal cords such that the vocal cords to be observed seem still.

However, in the laryngo-stroboscopy, in order to detect the vibration periods of the vocal cords, voice produced by a participant needs to be acquired, resulting in complications of the endoscope system. In addition, the participant needs to continue to produce the voice at a certain pitch for a certain time period.

As a countermeasure, in the endoscope system 11, the illumination light beams are applied by the pulsed-light emissions to the vocal cords as the photographic subject. With this, the vibration periods of the vocal cords, that is, the frequency of the vibration is detected on the basis of the input images obtained by capturing the vocal cords. In this way, the still images of the vocal cords are obtained as the output images.

In this case, in the same periods as the periods of the detected vibration of the vocal cords, that is, in synchronization with the vibration of the vocal cords, the pulsed-light emissions, that is, stroboscopic lighting by the light source device 23 is performed. With this, the still images of the vocal cords can be more easily obtained.

Figure 18:
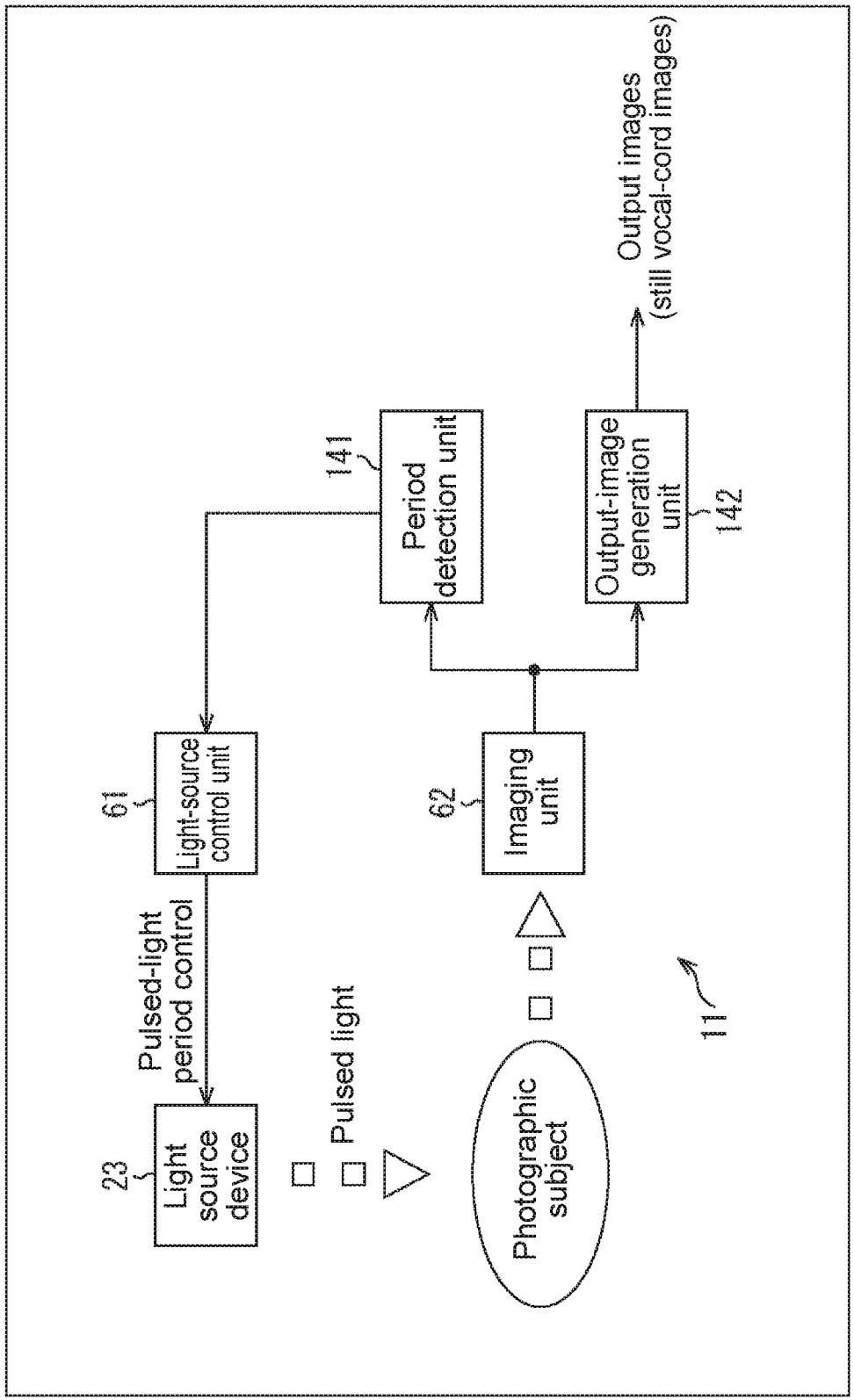
FIG. 18 A diagram showing another functional configuration example of the endoscope system.

The endoscope system 11 at a time of performing such vocal-cord observation is functionally configured, for example, as shown in FIG. 18. Note that, in FIG. 18, components corresponding to those in the case of FIG. 2 are denoted by the same reference symbols, and description thereof is omitted as appropriate.

In the example shown in FIG. 18, the endoscope system 11 includes the light-source control unit 61, the light source device 23, the imaging unit 62, a period detection unit 141, and an output-image generation unit 142.

Further, in this example, the light-source control unit 61 corresponds, for example, to the light-source control device 31 shown in FIG. 1, and the imaging unit 62 corresponds to the camera head 22 shown in FIG. 1. Further, the detection unit 33 in FIG. 1 functions as the period detection unit 141, and the signal processing circuit 32 in FIG. 1 functions as the output-image generation unit 142.

The light source device 23 performs the pulsed-light emissions in predetermined periods under the control by the light-source control unit 61 so as to apply pulsed light beams as the illumination light beams to the photographic subject. Specifically, the controlled light-source device 23 performs the pulsed-light emission a plurality of times in one-frame time period corresponding to the input image.

When the illumination light beams are applied to the vocal cords as the photographic subject, these illumination light beams turn into the reflected light beams by being reflected by the vocal cords, and then enter the imaging unit 62.

The imaging unit 62 takes the input images depicting the vocal cords as the photographic subject by receiving and photoelectrically converting the reflected light beams from the vocal cords. Then, the imaging unit 62 supplies the obtained input images to the period detection unit 141 and the output-image generation unit 142.

The period detection unit 141 detects, on the basis of the input images at respective time points, which are supplied from the imaging unit 62, the vibration periods of the vocal cords, that is, the frequency of the vibration of the vocal cords as motions of the photographic subject. Then, the period detection unit 141 supplies results of the detection as motion information items indicating the detection results of the motions of the vocal cords to the light-source control unit 61.

For example, the light source device 23 performs the pulsed-light emission the plurality of times in the one-frame time period corresponding to each of the input images, and the vocal cords also vibrate a plurality of times in the one-frame time period. Thus, the multiple exposure is performed at the time of taking each of the input images, and hence a plurality of images of the same photographic subject are contained in each of the input images.

Figure 19:
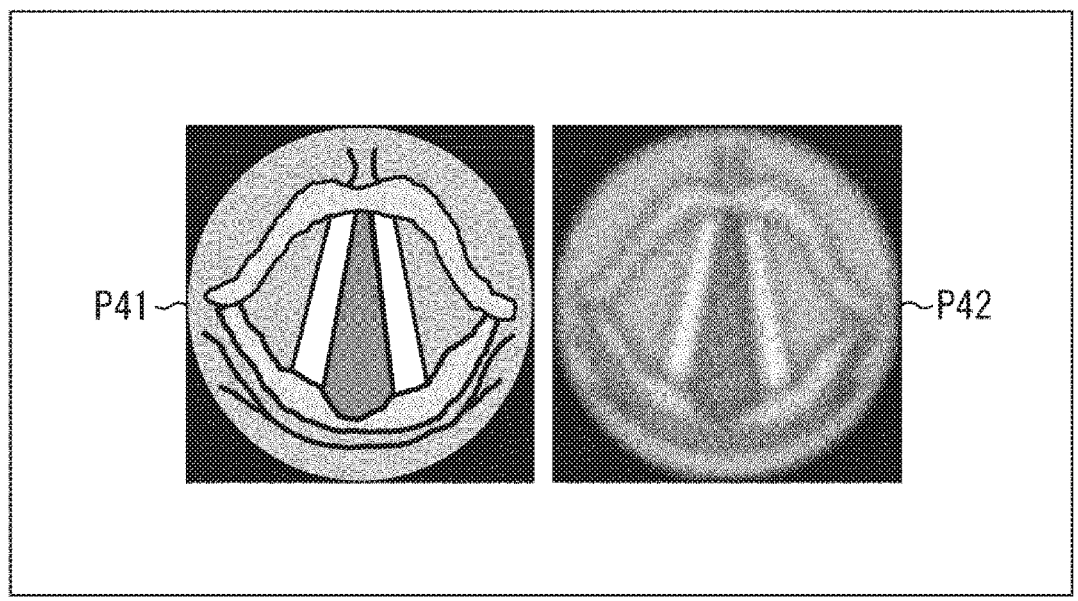
FIG. 19 An explanatory view illustrating blurring of an input image of vocal cords as a photographic subject.

Thus, when the periods of the pulsed-light emissions by the light source device 23, that is, a flashing frequency at which the illumination light beams are turned ON/OFF and the frequency of the vibration of the vocal cords are the same as each other, as illustrated in FIG. 19, for example, a high-contrast input image P41 is obtained.

The input image P41 illustrated in FIG. 19 is a high-contrast unblurred image of the vocal cords being the photographic subject. In other words, in the input image P41 to be obtained, the vocal cords as the photographic subject are depicted substantially in a stationary state.

This is because, when the frequency of the pulsed-light emissions and the frequency of the vibration of the vocal cords are the same as each other, images of the vocal cords at respective time points in the input image P41, that is, at times of respective ones of the pulsed-light emissions are superimposed on each other. For this reason, the image of the photographic subject does not blur.

In contrast, when the frequency of the pulsed-light emissions by the light source device 23 and the frequency of the vibration of the vocal cords are shifted from each other, positions of the images of the vocal cords (photographic subject) in the input image are also shifted from each other. Thus, for example, a low-contrast image such as an input image P42 in FIG. 19 is obtained.

As long as the frequency of the pulsed-light emissions and the frequency of the vibration of the vocal cords are different from each other, when the pulsed-light emission is performed the plurality of times in the one-frame time period, the positions of the vocal cords at the timings of the respective pulsed-light emissions are different from each other. Thus, positions of the images of the vocal cords in the input image P42 are also different from each other. In other words, a low-contrast blurred image including multiple images is obtained as the input image P42.

Referring back to the description with reference to FIG. 18, the period detection unit 141 detects the motions of the vocal cords, that is, the frequency of the vocal cords by utilizing a relationship between a degree of such frequency matching and the contrasts of the input images.

Specifically, for example, the period detection unit 141 calculates contrast evaluation values each representing a degree of a contrast of the input image obtained at each of the frequencies of the pulsed-light emissions, and detects a peak value of the contrast evaluation values from these contrast evaluation values obtained from the frequencies. Then, the period detection unit 141 determines one of the frequencies of the pulsed-light emissions, which corresponds to the peak value of the contrast evaluation values, as the frequency of the vibration of the vocal cords. The period detection unit 141 supplies an information item indicating the frequency or periods thereof as the motion information item being the detection result of the motion of the vocal cords as the photographic subject to the light-source control unit 61. The light-source control unit 61 changes the frequency, that is, the periods of the pulsed-light emission on the basis of the motion information item supplied from the period detection unit 141, and causes the light source device 23 to perform the light-emitting operation in the changed periods.

In particular, in the endoscope system 11, the stroboscopic lighting, that is, the pulsed-light emissions by the light source device 23 are performed in the plurality of different periods while gradually changing the frequency (periods) of the pulsed-light emissions. Then, the frequency of the vocal cords is detected from the contrast evaluation value obtained at each of the plurality of different frequencies (periods). Such a method of controlling the pulsed-light emissions is the same control method as contrast-type automatic focusing control including moving a lens so as to detect a lens position which corresponds to the peak value of the evaluation values of the contrasts. When this control method is employed, the frequency of the vibration of the vocal cords can be detected with high accuracy.

After the frequency of the vocal cords is detected as described above, the endoscope system 11 takes input images by performing the pulsed-light emissions at the same frequency as that indicated by the motion information item, that is, as the detected frequency. In this way, unblurred still output images of the vocal cords are obtained.

In other words, after the motion of the vocal cords as the photographic subject is detected, the input images taken by the imaging unit 62 are supplied to the output-image generation unit 142. The output-image generation unit 142 generates the output images by executing predetermined processes such as a gain control process on the input images supplied from the imaging unit 62, and then outputs these output images. The output images obtained in this way are the unblurred still images of the vocal cords.

<Yet Another Imaging Procedure>

Next, a procedure that is executed by the endoscope system 11 at the time when the vocal-cord observation is performed is described. In other words, in the following, with reference to the flowchart of FIG. 20, yet another imaging procedure by the endoscope system 11 is described.

In Step S181, the light-source control unit 61 determines a new frequency of the pulsed-light emissions on the basis of previous frequencies of the pulsed-light emissions.

For example, when first light-emissions are performed, a preset certain frequency is determined as the frequency of the pulsed-light emissions. Further, for example, when the motion information item has not yet been supplied despite previous gradual increase in frequency of the pulsed-light emissions, in other words, when the frequency of the vocal cords has not yet been detected, a much higher frequency is determined as the new frequency of the pulsed-light emissions.

In Step S182, the light source device 23 performs the pulsed-light emissions. Specifically, the light-source control unit 61 controls the light source device 23 such that the light source device 23 performs the pulsed-light emissions at the frequency determined in Step S181. The light source device 23 performs the pulsed-light emissions at the predetermined frequency under the control by the light-source control unit 61. With this, in the time period of one frame corresponding to the input image, the illumination light beams are applied periodically to the vocal cords being the photographic subject. These illumination light beams turn into the reflected light beams by being reflected by the vocal cords, and then enter the imaging unit 62. Note that, at this time, the participant continuously produces the voice at the certain pitch.

In Step S183, the imaging unit 62 takes, for example, the input images each corresponding to one frame by receiving and photoelectrically converting the incident reflected-light beams from the vocal cords. The imaging unit 62 supplies the taken input images to the period detection unit 141.

In Step S184, the period detection unit 141 detects the motion of the vocal cords being the photographic subject on the basis of the input images supplied from the imaging unit 62.

Specifically, the period detection unit 141 calculates the contrast evaluation value on the basis of the input images, and detects the peak value of the contrast evaluation values from previously-calculated contrast evaluation values.

In Step S185, on the basis of the detection result of the motion in Step S184, that is, on the basis of the detection result of the peak value of the contrast evaluation values, the period detection unit 141 determines whether or not the frequency of the vocal cords has been detected. For example, when the peak value of the contrast evaluation values has been detected, it is determined that the frequency of the vocal cords has been detected.

When it is determined in Step S185 that the frequency of the vocal cords has not yet been detected, the procedure returns to Step S181, and the above-described processes are repeated. In this case, imaging is performed at a different pulsed-light emission frequency, and the contrast evaluation values are calculated.

In contrast, it is determined in Step S185 that the frequency of the vocal cords has been detected, the period detection unit 141 determines the frequency of the pulsed-light emissions, at which the peak value of the contrast evaluation values is obtained, as the frequency of the vocal cords, more specifically, the frequency of the vibration of the vocal cords. Then, the period detection unit 141 supplies the information item indicating the frequency of the vibration of the vocal cords as the motion information item indicating the detection result of the motion to the light-source control unit 61. Next, the procedure proceeds to Step S186. Note that, the period detection unit 141 has already grasped the frequency of the pulsed-light emissions at respective time points by the light source device 23.

In Step S186, the light-source control unit 61 sets a frequency of subsequent pulsed-light emissions to the frequency of the vocal cords, which is indicated by the motion information item, and controls the light source device 23 such that the light source device 23 performs the subsequent pulsed-light emissions at this frequency.

Then, in Step S187, the light source device 23 performs the pulsed-light emissions under the control by the light-source control unit 61. With this, the pulsed-light emissions of the illumination light beams at the same frequency as the frequency of the vibration of the vocal cords.

In Step S188, the imaging unit 62 takes the input images by receiving and photoelectrically converting the incident reflected-light beams from the vocal cords, and supplies the obtained input images to the output-image generation unit 142.

In Step S189, the output-image generation unit 142 generates the output images on the basis of the input images supplied from the imaging unit 62, and then outputs these output images. Then, the imaging procedure is ended. For example, the output images are generated by executing necessary processes such as white-balance adjustment and the gain adjustment on the input images as appropriate. The output images output from the output-image generation unit 142 are, for example, displayed on the monitor 26, or recorded in the recorder.

As described above, the endoscope system 11 performs the pulsed-light emission a plurality of times in one-frame time period while changing the frequency, and detects the frequency of the vibration of the vocal cords by calculating the contrast evaluation values of the taken input images. Then, the endoscope system 11 takes the input images by performing the pulsed-light emissions at the detected frequency. With this, the motionless still output images of the vocal cords are obtained.

By performing the pulsed-light emissions while changing the frequency, and by calculating the contrast evaluation values, the motion of the vocal cords being the photographic subject can be detected more easily and with higher accuracy.

In particular, in the endoscope system 11, it is unnecessary to collect the voice produced by the participant, and the frequency of the vibration of the vocal cords is detected from the contrasts of the images. Thus, the frequency of the vibration of the vocal cords can be detected easily with a simple configuration and with high accuracy.

In addition, in the endoscope system 11, even when the participant fluctuates the pitch of the voice halfway, by detecting again the frequency of the vibration of the vocal cords and adjusting the frequency of the pulsed-light emissions while taking the input images, it is possible to follow the fluctuation of the pitch of the voice of the participant.

Incidentally, in the example described hereinabove, the output images of the vocal cords in the stationary state are generated by setting the frequency of the pulsed-light emissions the same as the frequency of the vibration of the vocal cords.

Figure 21:
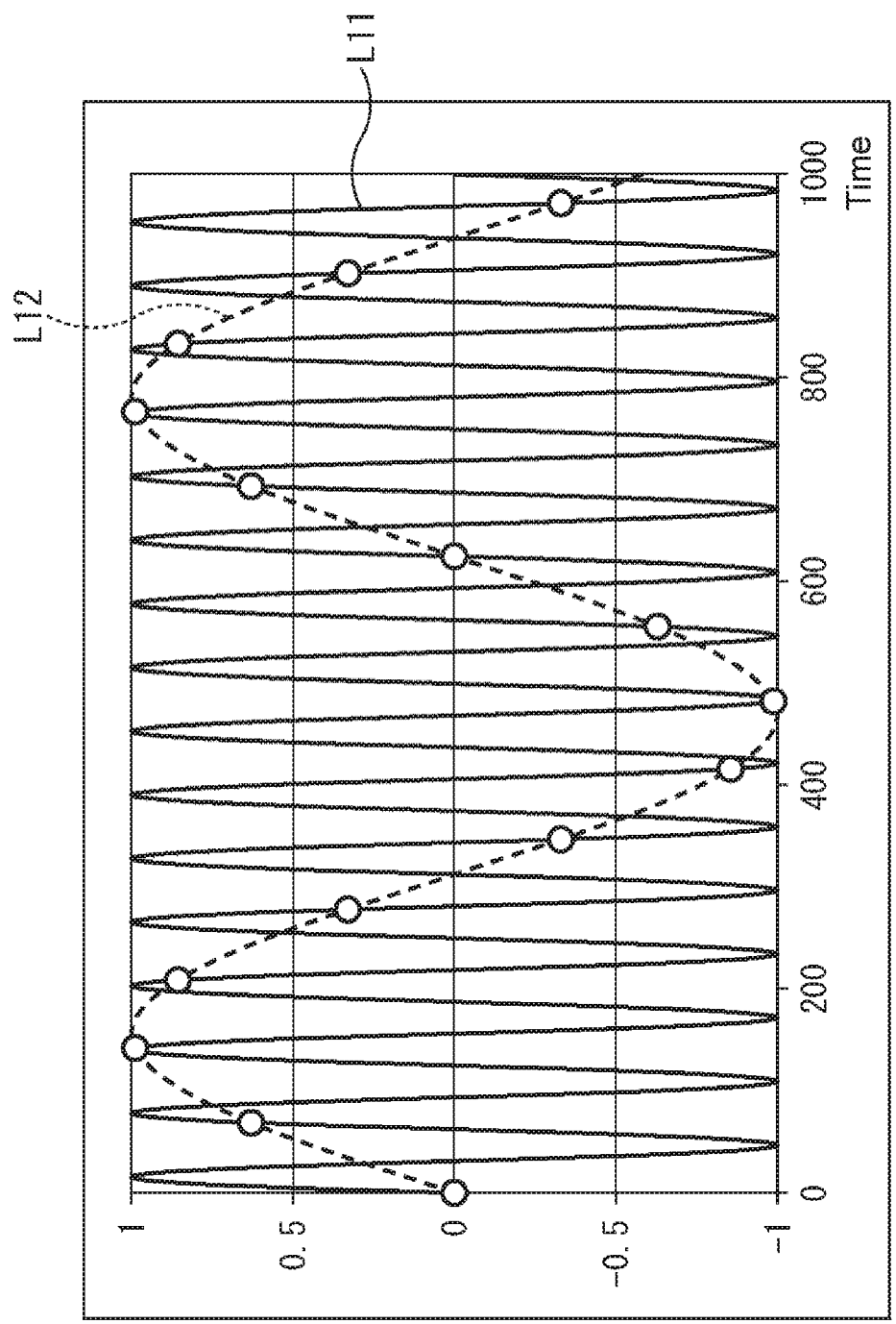
FIG. 21 An explanatory graph showing another example of an output image.

However, when the frequency of the pulsed-light emissions is slightly shifted from the frequency of the vibration of the vocal cords, as shown in FIG. 21, for example, a moving image in which the vocal cords appear to vibrate slowly, that is, a moving image in which the vibration of the vocal cords appears to be reproduced in slow motion can be obtained as the output images. Note that, in FIG. 21, the abscissa axis represents time, and the ordinate axis represents positions of the vocal cords.

In the example shown in FIG. 21, a curve L11 represents positions of the vocal cords at respective time points. Further, circles in FIG. 21 represent timings of the pulsed-light emissions, and a curve L12 represents positions of the vocal cords at respective time points, which are observed in the output images.

In this example, as understood from the curve L11, the vocal cords of the participant vibrate in certain periods, that is, at a certain frequency. Meanwhile, as understood from positions of the circles, in the endoscope system 11, the pulsed-light emissions are performed at a certain frequency different from the frequency of the vocal cords.

With this, the positions of the vocal cords in the input images correspond to the positions of the circles on the curve L11. As a result, the positions of the vocal cords at the respective time points, which are observed in the output images being the moving image, corresponds to the positions represented by the curve L12. Thus, the curve L12 can also be interpreted as a curve representing periods (frequency) of seeming vibration of the vocal cords in the output images.

When the frequency of the pulsed-light emissions is slightly shifted from the frequency of the vibration of the vocal cords as described above, the input images are exposed only at the timings represented by the circles. Thus, the output images in which the vocal cords, which are to vibrate in the periods represented by the curve L11, appear to vibrate in the periods represented by the curve L12 can be obtained. In other words, the moving image reproducing substantially in slow motion the motions of the vocal cords can be obtained as the output images.

Figure 20:
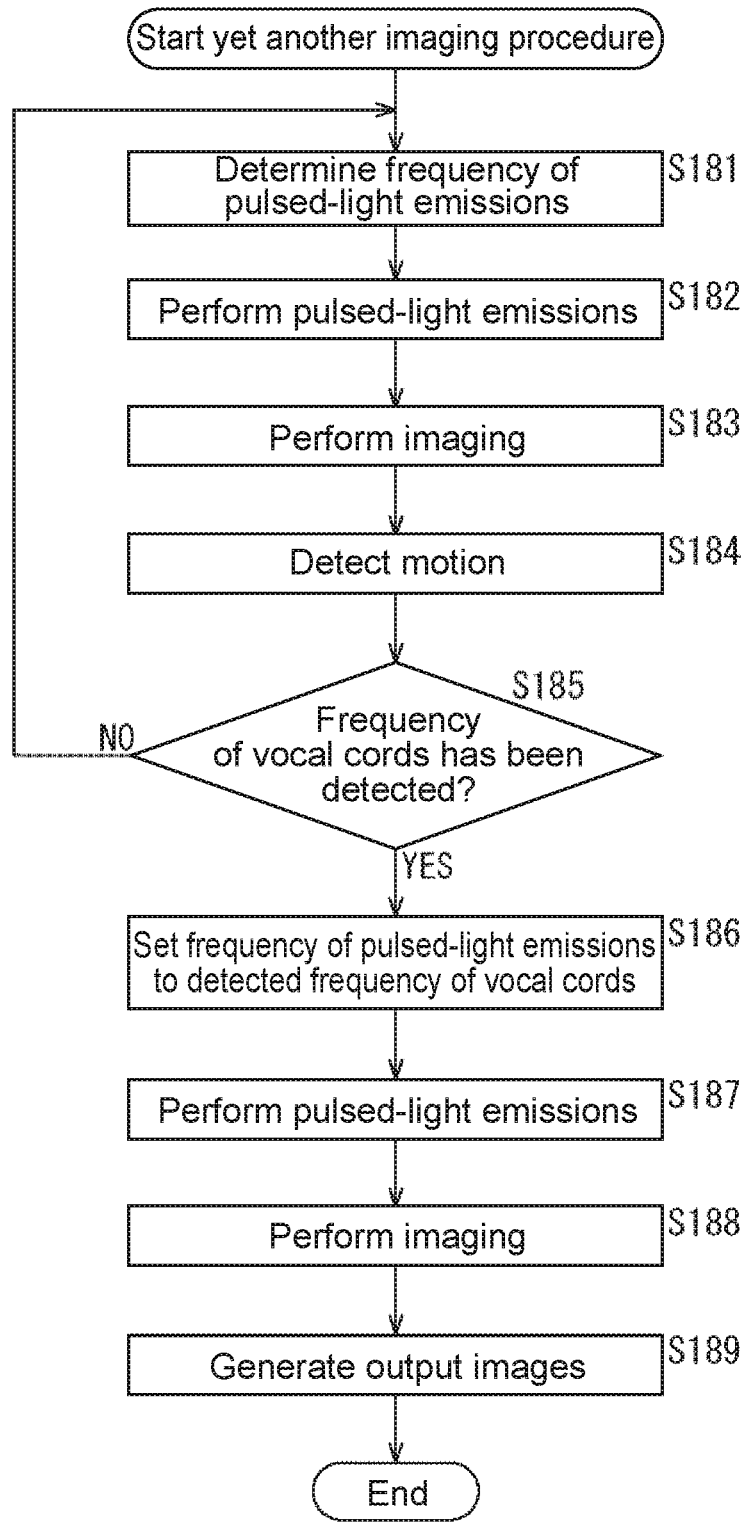
FIG. 20 An explanatory flowchart showing yet another imaging procedure.

In this case, it is only necessary to set, in Step S186 of the yet another imaging procedure described with reference to FIG. 20, a frequency shifted by a predetermined value from the detected frequency of the vocal cords as the frequency of the pulsed-light emissions. At this time, by properly controlling the frequency of the pulsed-light emissions, a rate of the motions of the vocal cords, which are reproduced in the output images, can be adjusted to a desired rate.

When the vocal-cord observation, that is, the laryngostroboscopy is performed with use of the endoscope system 11 as described above, without use of the configuration for collecting the voice of the participant, and detecting a frequency of the voice, still vocal cords, and vocal cords that slowly move can be observed. Further, the observation that enables even the pitch fluctuated halfway by the participant to be followed can be performed.

In addition, the present technology described hereinabove is advantageous also in detection of motions much more rapid than time intervals on a frame-by-frame basis, such as detection of a pulse wave velocity of a blood vessel, and motion detection by laser speckle imaging.

<Configuration Example of Endoscopic Surgical System>

Figure 22:
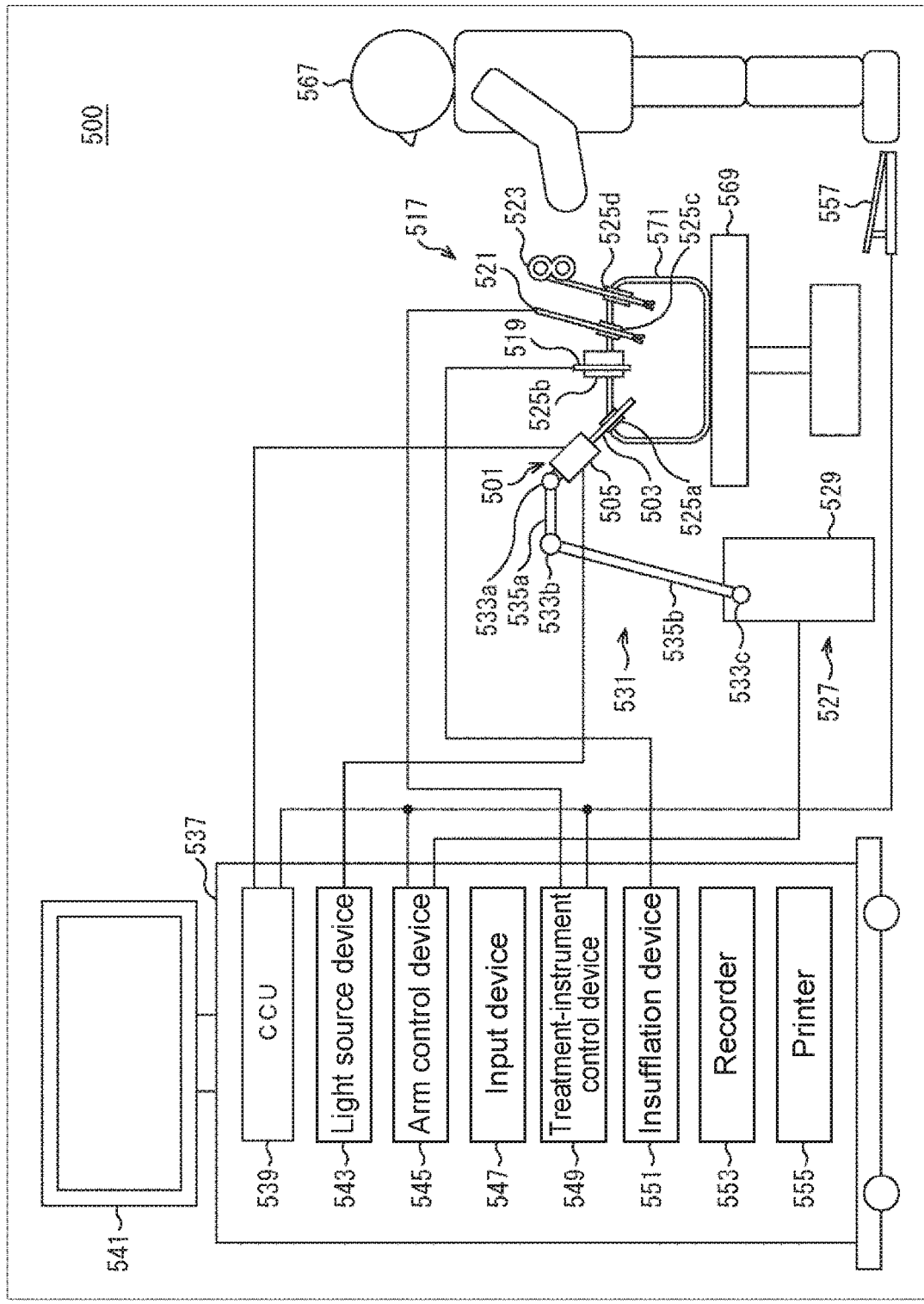
FIG. 22 A diagram showing a configuration example of an endoscopic surgical system.

Further, the present technology is applicable, for example, also to an endoscopic surgical system for performing endoscopic surgery with use of the endoscope system 11 shown in FIG. 1. In such a case, the endoscopic surgical system is configured, for example, as shown in FIG. 22. In other words, FIG. 22 is a diagram showing an example of a schematic configuration of an endoscopic surgical system 500 to which the technology according to the present disclosure is applicable.

FIG. 22 shows a state in which an operator (doctor) 567 performs surgery on a patient 571 on a patient bed 569 with use of the endoscopic surgical system 500. As shown in FIG. 22, the endoscopic surgical system 500 is constituted by an endoscope 501, other surgical instruments 517, a support arm device 527 that supports the endoscope 501, and a cart 537 to which various devices for the endoscopic surgery are mounted.

In the endoscopic surgery, an abdominal-wall incision is not performed. Instead, abdominal-wall puncture with a plurality of barrel-like opening instruments called trocars 525a to 525d is performed. Then, through the trocars 525a to 525d, a lens barrel 503 of the endoscope 501, and the other surgical instruments 517 are inserted into a body cavity of the patient 571. In the example shown in FIG. 22, as the other surgical instruments 517, an insufflation tube 519, an energy treatment instrument 521, and forceps 523 are inserted into the body cavity of the patient 571. Further, the energy treatment instrument 521 is a treatment instrument that performs, for example, incision and dissection of tissue or blood-vessel sealing with high-frequency current or ultrasonic vibration. Note that, the surgical instruments 517 shown in FIG. 22 are merely examples, and various surgical instruments to be generally used in the endoscopic surgery, such as tweezers and a retractor, may be used as the surgical instruments 517.

Images of surgical parts in the body cavity of the patient 571 are taken with the endoscope 501, and displayed on a display device 541. While checking the images of the surgical parts in real time, which are displayed on the display device 541, the operator 567 performs treatment such as resection of affected parts with use of the energy treatment instrument 521 and the forceps 523. Note that, although not shown, during the surgery, the insufflation tube 519, the energy treatment instrument 521, and the forceps 523 are supported by the operator 567 or, for example, by an assistant.

(Support Arm Device)

The support arm device 527 includes an arm portion 531 that extends from a base portion 529. In the example shown in FIG. 22, the arm portion 531, which is constituted by joint portions 533a, 533b, and 533c, and links 535a and 535b, is driven under control by an arm control device 545. The endoscope 501 is controlled in position and posture by being supported by the arm portion 531. With this, the endoscope 501 is stably fixed in position.

(Endoscope)

The endoscope 501 is constituted by the lens barrel 503, which is inserted into the body cavity of the patient 571 in a region over a predetermined length from its distal end, and by a camera head 505 that is connected to a proximal end of the lens barrel 503. The endoscope 501 in the example shown in FIG. 22 is constituted as what is called a rigid scope, that is, the lens barrel 503 thereof is rigid. However, the endoscope 501 may be constituted as what is called a flexible scope, that is, the lens barrel 503 may be flexible.

An opening portion into which an objective lens is fitted is provided at the distal end of the lens barrel 503. A light source device 543 is connected to the endoscope 501. Light beams generated by the light source device 543 are guided to the distal end of the lens barrel 503 by a light guide extended in the lens barrel, and are applied through the objective lens to an observation target in the body cavity of the patient 571. Note that, the endoscope 501 may be a forward-viewing endoscope, a forward-oblique viewing endoscope, or a side-viewing endoscope.

An optical system and an imaging element are provided in the camera head 505, and reflected light beams (observation light beams) from the observation target are converged to the imaging element by the optical system. The observation light beams are photoelectrically converted by the imaging element such that electrical signals corresponding to the observation light beams, that is, image signals corresponding to observation images are generated. These image signals are transmitted as RAW data items to a CCU (Camera Control Unit) 539. Note that, a function to adjust a magnification and a focal length by driving the optical system as appropriate is provided to the camera head 505.

For example, in order to perform stereoscopic viewing (three-dimensional representation), a plurality of imaging elements may be provided in the camera head 505. In this case, in the lens barrel 503, in order that the observation light beams are guided to each of the plurality of imaging elements, a plurality of relay optical systems are provided.

(Various Devices that are Mounted to Cart)

The CCU 539, which is constituted, for example, by a CPU (Central Processing Unit) and a GPU (Graphics Processing Unit), collectively controls the operations of the endoscope 501 and the display device 541. Specifically, the CCU 539 executes, on the image signals received from the camera head 505, various image processes for displaying images in response to the image signals, such as a development process (demosaic process). The CCU 539 provides, to the display device 541, the image signals that have been subjected to the image processes. Further, the CCU 539 controls and drives the camera head 505 by transmitting control signals thereto. These control signals include information items of imaging conditions such as the magnification and the focal length.

Under the control by the CCU 539, the display device 541 displays images in response to the image signals that have been subjected to the image processes by the CCU 539. When the endoscope 501 corresponds, for example, to high-resolution imaging such as 4K (3,840 horizontal pixels×2,160 vertical pixels) or 8K (7,680 horizontal pixels×4,320 vertical pixels), and/or to the three-dimensional representation, a display device capable of high-resolution representation, and/or a display device capable of the three-dimensional representation can be used correspondingly thereto respectively as the display device 541. When the display device 541 to be used corresponds to the high-resolution imaging such as 4K or 8K, and has a size of 55 inches or more, a greater sense of immersion can be obtained. Further, depending on uses, the display device 541 to be provided may include a plurality of display devices 541 having different resolutions and sizes.

The light source device 543, which is constituted, for example, by a light source such as an LED, supplies the illumination light beams at the time of imaging the surgical parts to the endoscope 501.

The arm control device 545, which is constituted, for example, by a processor such as the CPU, is operated in accordance with a predetermined program. With this, the arm portion 531 of the support arm device 527 is controlled and driven in accordance with a predetermined control method.

An input device 547 is an input/output interface with respect to the endoscopic surgical system 500. A user can input, via the input device 547, various information items and instructions to the endoscopic surgical system 500. For example, the user inputs, via the input device 547, various information items of the surgery, such as physical information items of the patient, and information items of a surgical procedure. Further, for example, the user inputs, via the input device 547, instructions such as an instruction to drive the arm portion 531, an instruction to change the conditions of imaging (such as a type of the illumination light beams, the magnification, and the focal length) by the endoscope 501, and an instruction to drive the energy treatment instrument 521.

Types of the input device 547 are not limited. The input device 547 may be various known input devices. For example, a mouse, a keyboard, a touchscreen, a switch, a foot switch 557, and/or a lever is applicable to the input device 547. When the touchscreen is used as the input device 547, this touchscreen may be provided on a display surface on the display device 541.

Alternatively, the input device 547 may be a device to be worn by the user, such as an eyeglass-type wearable device or an HMD (Head Mounted Display). Various inputs are performed by detection with these devices, specifically, by gestures or lines of sight of the user. Further, the input device 547 includes a camera capable of detecting a motion of the user such that the various inputs are performed by detection from a video taken by the camera, specifically, by the gestures or the lines of sight of the eyes of the user. In addition, the input device 547 includes a microphone capable of collecting voice of the user such that the various inputs are performed by the voice via the microphone. When the input device 547 is configured to be capable of enabling the various information items to be input in a hands-free manner in this way, the user (such as operator 567) who is in a clean area, in particular, is enabled to operate devices in a dirty area in the hands-free manner. Further, the user is enabled to operate these devices without releasing a surgical instrument in his/her hand. Thus, convenience of the user is increased.

A treatment-instrument control device 549 controls and drives the energy treatment instrument 521 for, for example, cauterization and the incision of tissue or the blood-vessel sealing. An insufflation device 551 feeds a gas into the body cavity of the patient 571 through the insufflation tube 519 so as to insufflate the body cavity for purposes of securing a field of vision of the endoscope 501 and securing a working space for the operator. A recorder 553 is a device capable of recording the various information items of the surgery. A printer 555 is a device capable of printing the various information items of the surgery into various forms such as a text, an image, or a graph.

Further, there are correspondences as follows between the endoscopic surgical system 500 shown in FIG. 22 and the endoscope system 11 shown in FIG. 11. Specifically, the lens barrel 503 corresponds to the scope 21, and the camera head 505 corresponds to the camera head 22. Further, the light source device 543 corresponds to the light source device 23, the camera control unit 539 corresponds to the camera control unit 24, the input device 547 corresponds to the operation input device 25, and the display device 541 corresponds to the monitor 26.

Hereinabove, an example of the endoscopic surgical system 500 to which the technology according to the present disclosure is applicable is described. Note that, the system to which the technology according to the present disclosure is applicable is not limited to the example described hereinabove of the endoscopic surgical system 500. For example, the technology according to the present disclosure may be applied to an inspection flexible-endoscope system or a microscopic operation system.

<Configuration Example of Computer>

Incidentally, the above-described series of processes may be executed by hardware or by software. At a time of executing the series of processes by the software, programs of the software are installed in the computer. Examples of the computer include a computer incorporated in dedicated hardware, and a general-purpose computer capable of exerting various functions in accordance with various programs installed therein.

Figure 23:
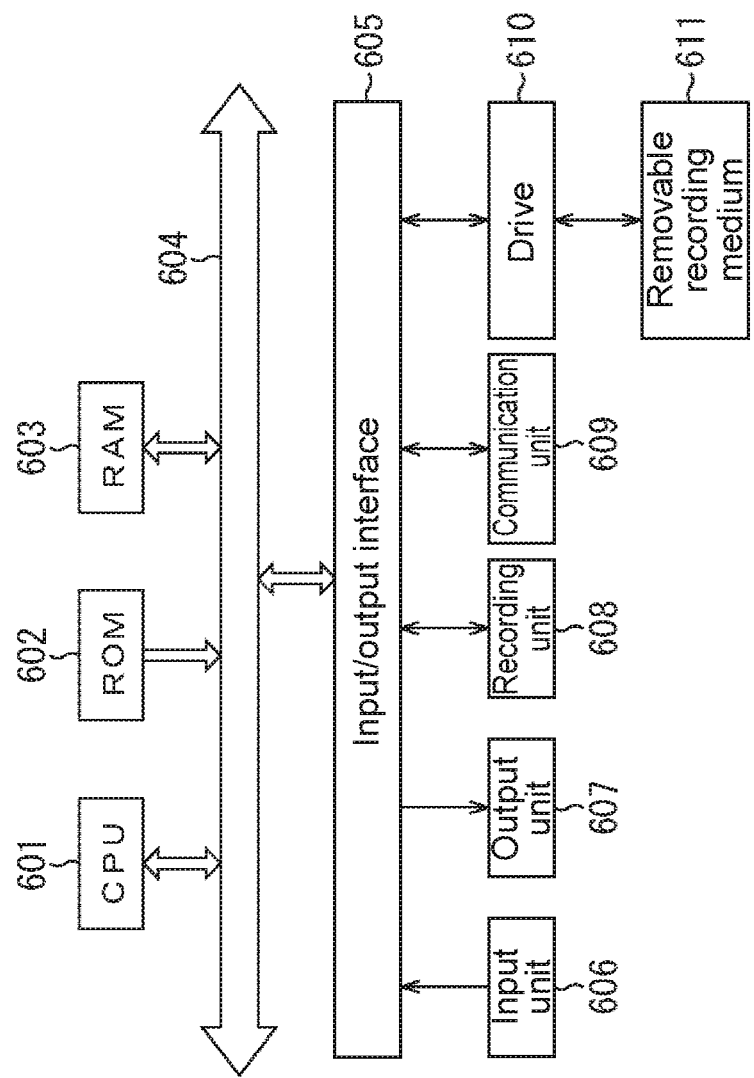
FIG. 23 A diagram showing a configuration example of a computer.

FIG. 23 is a block diagram showing a configuration example of the hardware of a computer that executes the above-described series of processes in accordance with the programs.

In the computer, a CPU 601, a ROM (Read Only Memory) 602, and a RAM (Random Access Memory) 603 are connected to each other via a bus 604.

An input/output interface 605 is also connected to the bus 604. An input unit 606, an output unit 607, a recording unit 608, a communication unit 609, and a drive 610 are connected to the input/output interface 605.

The input unit 606 includes a keyboard, a mouse, a microphone, and an imaging element. The output unit 607 includes a display and a speaker. The recording unit 608 includes a hard disk and a nonvolatile memory. The communication unit 609 includes a network interface. The drive 610 drives removable recording media 611 such as a magnetic disk, an optical disk, a magneto-optical disk, or a semiconductor memory.

In the computer configured as described above, for example, the CPU 601 loads a program recorded in the recording unit 608 to the RAM 603 via the input/output interface 605 and the bus 604, and executes the program. In this way, the above-described series of processes is executed.

The program to be executed by the computer (CPU 601) may be provided, for example, by being recorded in the removable recording medium 611 in a form of a packaged medium or the like. Alternatively, the program may be provided via wired or wireless transmission media such as a local area network, the Internet, and digital satellite broadcasting.

In the computer, the program may be installed into the recording unit 608 via the input/output interface 605 from the removable recording medium 611 loaded to the drive 610. Alternatively, the program may be installed into the recording unit 608 by being received by the communication unit 609 via wired and wireless transmission media. Still alternatively, the program may be pre-installed in the ROM 602 or the recording unit 608.

Note that, the program to be executed by the computer may be programs for executing the processes in time series in the order described herein, or may be programs for executing the processes parallel to each other or at necessary timings, for example, when being called.

In addition, the embodiments of the present technology are not limited to the above-described embodiments, and various modifications may be made thereto without departing from the essence of the present technology.

For example, the present technology may have a configuration of cloud computing in which one function is shared by a plurality of devices via a network and processed in cooperation with each other.

Further, Steps described above with reference to the flowcharts may be executed by a single device, or may be executed by a plurality of devices in a shared manner.

Still further, when a plurality of processes are contained in a single Step, the plurality of processes contained in the single Step may be executed by a single device, or may be executed by a plurality of devices in a shared manner.

Yet further, the advantages described herein are merely examples, and hence are not limited thereto. Thus, other advantages may be obtained.

Yet further, the present technology may also employ the following configurations.

(1)

An image processing device, including:

a light-source control unit that controls a light source such that the light source performs a pulsed-light emission a plurality of times in an exposure time period of each captured image; and a motion detection unit that detects a motion of a photographic subject in the captured images.

(2)

The image processing device according to Item (1), in which the captured images are images of a living body.

(3)

The image processing device according to Item (1) or (2), in which the motion detection unit detects, as the motion, magnitudes of components of a motion vector on the basis of one of the captured images.

(4)

The image processing device according to Item (3), in which the light-source control unit controls the light source such that the light source outputs light beams containing the same wavelength component at times of the pulsed-light emissions.

(5)

The image processing device according to Item (4), in which the motion detection unit further detects, as the motion, a direction of the motion vector on the basis of a plurality of the captured images.

(6)

The image processing device according to Item (4) or (5), further including a motion correction unit that performs motion correction with respect to the captured images on the basis of a result of the detection of the motion.

(7)

The image processing device according to Item (3) or (4), further including an image generation unit that generates images of the photographic subject from other ones of the captured images on the basis of a result of the detection of the motion, the other ones of the captured images being at time points when the motion is not made.

(8)

The image processing device according to Item (4) or (5), in which the light-source control unit controls the light source such that exposure time periods in each of which the light beam containing the wavelength component is continuously output, and other exposure time periods in each of which the pulsed-light emission is performed the plurality of times are provided.

(9)

The image processing device according to Item (8), in which the motion detection unit detects the motion on the basis of ones of the captured images, the ones of the captured images corresponding to the other exposure time periods in each of which the pulsed-light emission is performed the plurality of times, and the image processing device further includes a motion correction unit that performs motion correction with respect to other ones of the captured images on the basis of a result of the detection of the motion, the other ones of the captured images corresponding to the exposure time periods in each of which the light beam containing the wavelength component is continuously output.

(10)

The image processing device according to Item (8) or (9), in which the light-source control unit controls the light source such that the exposure time periods in each of which the light beam containing the wavelength component is continuously output, and the other exposure time periods in each of which the pulsed-light emission is performed the plurality of times are provided alternately to each other.

(11)

The image processing device according to Item (8) or (9), in which the light-source control unit controls the light source such that the other exposure time periods in each of which the pulsed-light emission is performed the plurality of times are provided at unequal intervals.

(12)

The image processing device according to Item (1) or (2), in which the light-source control unit controls the light source such that the light source outputs light beams containing wavelength components different from each other respectively at times of the plurality of times of pulsed-light emissions.

(13)

The image processing device according to Item (12), in which the motion detection unit detects, as the motion, a motion vector on the basis of images respectively containing the wavelength components, the images respectively containing the wavelength components being obtained from one of the captured images.

(14)

The image processing device according to any one of Items (1) to (3), in which the light-source control unit controls another light source different from the light source such that the other light source continuously outputs a light beam containing a predetermined wavelength component during an exposure time period of each input image of the photographic subject, the input images being different from the captured images, and controls the light source such that the light source outputs light beams containing another wavelength component different from the predetermined wavelength component by performing the pulsed-light emission the plurality of times in a time period including at least a part of the exposure time period of each of the input images, and the image processing device further includes a first imaging unit that takes the captured images, a second imaging unit that takes the input images, and a splitting element that optically splits the light beams from the photographic subject, inputs ones of the split light beams to the first imaging unit, and inputs other ones of the split light beams to the second imaging unit.

(15)

The image processing device according to Item (14), further including a motion correction unit that performs motion correction with respect to the input images on the basis of a result of the detection of the motion.

(16)

The image processing device according to Item (1) or (2), in which the light-source control unit controls the light source such that the light source performs the pulsed-light emissions in a plurality of different periods while changing periods of the pulsed-light emissions, and the motion detection unit detects, as the motion, a vibration period of the photographic subject on the basis of degrees of contrasts of the captured images obtained respectively in the plurality of different periods.

(17)

The image processing device according to Item (16), in which the light-source control unit causes, after the detection of the motion, the light source to perform the pulsed-light emissions in a period in accordance with a result of the detection of the motion.

(18)

An image processing method, including the steps of:

controlling a light source such that the light source performs a pulsed-light emission a plurality of times in an exposure time period of each captured image; and detecting a motion of a photographic subject in the captured images.

(19)

A program for causing a computer to execute a procedure including the steps of:

controlling a light source such that the light source performs a pulsed-light emission a plurality of times in an exposure time period of each captured image; and detecting a motion of a photographic subject in the captured images.

(20)

An endoscope system, including: a light source capable of performing a pulsed-light emission; a light-source control unit that controls the light source such that the light source performs the pulsed-light emission a plurality of times in an exposure time period of each captured image; an imaging unit that takes the captured images; and a motion detection unit that detects a motion of a photographic subject in the captured images.

REFERENCE SIGNS LIST 11 endoscope system
21 scope
22 camera head
23 light source device
24 camera control unit
26 monitor
31 light-source control device
32 signal processing circuit
33 detection unit
61 light-source control unit
62 imaging unit
63 motion detection unit
64 output-image generation unit
141 period detection unit
142 output-image generation unit

The invention claimed is:

1. An image processing device, comprising:
a central processing unit (CPU) configured to:
control a first light source to perform a pulsed-light emission a plurality of times in a first exposure time period of each captured image of a plurality of captured images;
detect a motion of a photographic subject in the plurality of captured images, wherein the motion is detected as magnitudes of components of a motion vector based on a first captured image of the plurality of captured images; and
generate a first set of images of the photographic subject from at least one second captured image of the plurality of captured images based on a result of the detection of the motion, wherein the at least one second captured image is captured at a time point at which the motion is not made.

2. The image processing device according to claim 1, wherein the plurality of captured images corresponds to images of a living body.

3. The image processing device according to claim 1, wherein the CPU is further configured to control the first light source to output light beams containing same wavelength component at the plurality of times of the pulsed-light emission.

4. The image processing device according to claim 3, wherein the CPU is further configured to detect, as the motion, a direction of the motion vector based on the plurality of captured images.

5. The image processing device according to claim 3, wherein the CPU is further configured to perform motion correction with respect to the plurality of captured images based on the result of the detection of the motion.

6. The image processing device according to claim 3, wherein the CPU is further configured to control the first light source to:

continuously output the light beams containing the same wavelength component in a second exposure time period, and
perform the pulsed-light emission the plurality of times in the first exposure time period.

7. The image processing device according to claim 6, wherein
the CPU is further configured to:
detect the motion based on the first captured image of the plurality of captured images,
wherein the first captured image of the plurality of captured images corresponds to the first exposure time period in which the pulsed-light emission is performed the plurality of times; and
perform motion correction with respect to the at least one second captured image of the plurality of captured images based on the result of the detection of the motion,
wherein the at least one second captured image of the plurality of captured images corresponds to the second exposure time period in which the light beams containing the same wavelength component are continuously output.

8. The image processing device according to claim 6, wherein the CPU is further configured to control the first light source to alternatively provide the second exposure time period in which the light beams containing the same wavelength component are continuously output, and the first exposure time period in which the pulsed-light emission is performed the plurality of times.

9. The image processing device according to claim 6, wherein the CPU is further configured to control the first light source to provide a plurality of first exposure time periods, in each of which the pulsed-light emission is performed the plurality of times, at unequal intervals.

10. The image processing device according to claim 1, wherein the CPU is further configured to control the first light source to output light beams containing different wavelength components at the plurality of times of the pulsed-light emission.

11. The image processing device according to claim 10, wherein
the CPU is further configured to detect, as the motion, the motion vector based on a first plurality of images of the plurality of captured images containing the different wavelength components, and
each image of the first plurality of images is obtained from the first captured image of the plurality of captured images.

12. The image processing device according to claim 1, wherein
the CPU is further configured to:
control a second light source different from the first light source to continuously output a first light beam containing a specific wavelength component during a second exposure time period of each input image of a plurality of input images of the photographic subject, wherein the plurality of input images is different from the plurality of captured images; and
control the first light source to output light beams containing a wavelength component different from the specific wavelength component by performing the pulsed-light emission the plurality of times in a time period including at least a part of the second exposure time period of each input image of the plurality of input images, and the image processing device further includes:
- a first camera configured to take the plurality of captured images,
- a second camera configured to take the plurality of input images, and
- a splitting element configured to:
  - optically split the light beams from the photographic subject,
  - input at least one first light beam of the split light beams to the first camera, and
  - input at least one second light beam of the split light beams to the second camera, wherein the at least one second light beam is different from the at least one first light beam.

13. The image processing device according to claim 12, wherein the CPU is further configured to perform motion correction with respect to the plurality of input images based on the result of the detection of the motion.

14. The image processing device according to claim 1, wherein the CPU is further configured to:
- control the first light source to perform the pulsed-light emission in a plurality of different periods while changing periods of the pulsed-light emission; and
- detect, as the motion, a vibration period of the photographic subject based on degrees of contrasts of the plurality of captured images obtained respectively in the plurality of different periods.

15. The image processing device according to claim 14, wherein the CPU is further configured to cause, after the detection of the motion, the first light source to perform the pulsed-light emission in the detected vibration period based on the result of the detection of the motion.

16. An image processing method, comprising:
- controlling a light source to perform a pulsed-light emission a plurality of times in an exposure time period of each captured image of a plurality of captured images;
- detecting a motion of a photographic subject in the plurality of captured images, wherein the motion is detected as magnitudes of components of a motion vector based on a first captured image of the plurality of captured images; and
- generating a set of images of the photographic subject from at least one second captured image of the plurality of captured images based on a result of the detection of the motion, wherein the at least one second captured image is captured at a time point at which the motion is not made.

17. A non-transitory computer-readable medium having stored thereon, computer-executable instructions, which when executed by a computer, cause the computer to execute operations, the operations comprising:
- controlling a light source to perform a pulsed-light emission a plurality of times in an exposure time period of each captured image of a plurality of captured images;
- detecting a motion of a photographic subject in the plurality of captured images, wherein the motion is detected as magnitudes of components of a motion vector based on a first captured image of the plurality of captured images; and
- generating a set of images of the photographic subject from at least one second captured image of the plurality of captured images based on a result of the detection of the motion, wherein the at least one second captured image is captured at a time point at which the motion is not made.

18. An endoscope system, comprising:
- a light source configured to perform a pulsed-light emission;
- a camera configured to capture a plurality of images; and
- a central processing unit (CPU) circuitry configured to:
  - control the light source to perform the pulsed-light emission a plurality of times in an exposure time period of each captured image of the plurality of captured images;
  - detect a motion of a photographic subject in the plurality of captured images, wherein the motion is detected as magnitudes of components of a motion vector based on a first captured image of the plurality of captured images; and
  - generate a set of images of the photographic subject from at least one second captured image of the plurality of captured images based on a result of the detection of the motion, wherein the at least one second captured image is captured at a time point at which the motion is not made.

* * * * *